US008772030B2

(12) United States Patent
Giacomello et al.

(10) Patent No.: US 8,772,030 B2
(45) Date of Patent: *Jul. 8, 2014

(54) CARDIAC STEM CELLS AND METHODS FOR ISOLATION OF SAME

(75) Inventors: Alessandro Giacomello, Rome (IT); Elisa Messina, Rome (IT); Massimo Battaglia, Rome (IT); Giacomo Frati, Rome (IT)

(73) Assignee: Universita Degli Studi di Roma "La Sapienza", Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,788

(22) Filed: Sep. 26, 2011

(65) Prior Publication Data
US 2012/0020935 A1 Jan. 26, 2012

Related U.S. Application Data

(63) Continuation of application No. 10/567,008, filed as application No. PCT/IT2004/000421 on Jul. 29, 2004, now Pat. No. 8,268,619.

(30) Foreign Application Priority Data

Jul. 31, 2003 (IT) .............................. RM2003A0376

(51) Int. Cl.
*C12N 5/00* (2006.01)
*C12N 5/02* (2006.01)

(52) U.S. Cl.
USPC ............ 435/377; 435/379; 435/381; 435/383

(58) Field of Classification Search
USPC ............................ 435/377, 383, 325; 431/381
See application file for complete search history.

(56) References Cited

U.S. PATENT DOCUMENTS

| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |
| 5,052,402 A | 10/1991 | Bencini et al. |
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,165,164 A | 12/2000 | Hill et al. |

(Continued)

FOREIGN PATENT DOCUMENTS

| CN | 1537646 | 10/2004 |
| CN | 1772300 | 5/2006 |

(Continued)

OTHER PUBLICATIONS

Duff et al., "CD105 is important for angiogenesis: evidence and potential applications," FASEB J, Jun. 2003, vol. 17(9), pp. 984-992.
Gu, Bispecific Antibody Targeted Stem Cell Therapy for Myocardial Repair, University of California, San Francisco and University of California Berkeley, 2008.
Kyrtatos et al., Magnetic Tagging Increases Delivery of Circulating Progenitors in Vascular Injury, J. Am. Coll. Cardiol. Intv. 2:794-802 (2009).
Lee et al., Antibody Targeting of Stem Cells to Infarcted Myocardium, Stem Cells Translational and Clinical Research 25:712-717 (2007).
Levenberg, et al. Endothelial cells derived from human embryonic stem cells. Proceedings of the National Academy of Sciences Apr. 2, 2002, vol. 99, No. 7, pp. 4391-4396.
Lum et al., The New Face of Bispecific Antibodies: Targeting Cancer and Much More, Exp. Hematol. 34: 1-6 (2006).

(Continued)

*Primary Examiner* — Anoop Singh
(74) *Attorney, Agent, or Firm* — Knobbe Martens Olson & Bear, LLP

(57) ABSTRACT

Method for the isolation, expansion and preservation of cardiac stem cells from human or animal tissue biopsy samples to be employed in cell transplantation and functional repair of the myocardium or other organs. Cells may also be used in gene therapy for treating cardiomyopathies, for treating ischemic heart diseases and for setting in vitro models to study drugs.

11 Claims, 23 Drawing Sheets

(56) References Cited

U.S. PATENT DOCUMENTS

| | | |
|---|---|---|
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marban |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,562,972 B2 | 10/2013 | Edinger et al. |
| 2002/0061587 A1 | 5/2002 | Anversa |
| 2002/0098167 A1 | 7/2002 | Anversa et al. |
| 2002/0156383 A1 | 10/2002 | Altman et al. |
| 2002/0177772 A1 | 11/2002 | Altman et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0136966 A1 | 7/2004 | Anversa et al. |
| 2004/0153139 A1 | 8/2004 | Altman |
| 2004/0158313 A1 | 8/2004 | Altman |
| 2004/0168341 A1 | 9/2004 | Petersen et al. |
| 2005/0074880 A1 | 4/2005 | Sang et al. |
| 2005/0090732 A1 | 4/2005 | Ivkov |
| 2005/0176620 A1 | 8/2005 | Prestwich et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0020758 A1 | 1/2007 | Giacomello et al. |
| 2007/0048383 A1 | 3/2007 | Helmus |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0129296 A1 | 6/2007 | Zhou |
| 2007/0142774 A1 | 6/2007 | Rosenman |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0138416 A1 | 6/2008 | Rauh et al. |
| 2008/0187514 A1 | 8/2008 | Anversa |
| 2008/0267921 A1 | 10/2008 | Marban et al. |
| 2008/0268061 A1 | 10/2008 | Jordan et al. |
| 2008/0274998 A1 | 11/2008 | Cohen et al. |

(56) References Cited

U.S. PATENT DOCUMENTS

| | | |
|---|---|---|
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0123366 A1 | 5/2009 | Dobson et al. |
| 2009/0136582 A1 | 5/2009 | Albrecht et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1* | 3/2010 | Marban et al. ............... 435/381 |
| 2010/0081200 A1 | 4/2010 | Rajala et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0256105 A1 | 10/2011 | Marbán et al. |
| 2011/0256621 A1 | 10/2011 | Albrecht et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2013/0059006 A1 | 3/2013 | Schmuck et al. |
| 2013/0266543 A1 | 10/2013 | Nadal-Ginard |
| 2013/0288962 A1 | 10/2013 | Anversa et al. |
| 2013/0295060 A1 | 11/2013 | Yang et al. |
| 2013/0309304 A1 | 11/2013 | Nadal-Ginard |

FOREIGN PATENT DOCUMENTS

| | | |
|---|---|---|
| CN | 1785430 | 6/2006 |
| EP | 1254952 | 11/2002 |
| EP | 1970446 | 9/2008 |
| EP | 2182053 | 5/2010 |
| EP | 2228444 | 9/2010 |
| EP | 1631318 | 11/2010 |
| EP | 1650293 | 12/2010 |
| EP | 2371370 | 10/2011 |
| EP | 2385120 | 11/2011 |
| EP | 2446929 | 5/2012 |
| EP | 1945256 | 7/2012 |
| EP | 2094869 | 7/2012 |
| EP | 2486944 | 8/2012 |
| EP | 2277548 | 1/2013 |
| JP | 2005110565 | 4/2005 |
| KR | 100830889 | 5/2008 |
| WO | WO 97/05265 | 2/1997 |
| WO | WO 97/12912 | 4/1997 |
| WO | WO 98/04708 | 2/1998 |
| WO | WO 98/32866 | 7/1998 |
| WO | WO 99/11809 | 3/1999 |
| WO | WO 99/39624 | 8/1999 |
| WO | WO 99/49015 | 9/1999 |
| WO | WO 99/51297 | 10/1999 |
| WO | WO 00/09185 | 2/2000 |
| WO | WO 00/24452 | 5/2000 |
| WO | WO 01/10482 | 2/2001 |
| WO | WO 01/26585 | 4/2001 |
| WO | WO 01/26706 | 4/2001 |
| WO | WO 01/26727 | 4/2001 |
| WO | WO 01/48151 | 7/2001 |
| WO | WO 01/76679 | 10/2001 |
| WO | WO 01/76682 | 10/2001 |
| WO | WO 02/09650 | 2/2002 |
| WO | WO 02/13760 | 2/2002 |
| WO | WO 02/051489 | 7/2002 |
| WO | WO 03/006950 | 1/2003 |
| WO | WO 03/008535 | 1/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO2008/036776 | 3/2008 |
| WO | WO 2008/043521 | 4/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO2009/058818 | 5/2009 |
| WO | WO 2009/062143 | 5/2009 |
| WO | WO 2009/062169 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/056116 | 7/2009 |
| WO | WO2009/067644 | 8/2009 |
| WO | WO 2009/100137 | 8/2009 |
| WO | WO 2009/149956 | 12/2009 |
| WO | WO 2009/152111 | 12/2009 |
| WO | WO 2010/028090 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO2011/029092 | 3/2011 |
| WO | WO2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO2011/062244 | 5/2011 |
| WO | WO2011/064354 | 6/2011 |
| WO | WO2011/084460 | 7/2011 |
| WO | WO 2011/121120 | 10/2011 |
| WO | WO2011/127625 | 10/2011 |
| WO | WO 2011/138328 | 11/2011 |
| WO | WO2011/143499 | 11/2011 |
| WO | WO2012/020307 | 2/2012 |
| WO | WO2012/020308 | 2/2012 |
| WO | WO2012/055971 | 5/2012 |

(56) References Cited

FOREIGN PATENT DOCUMENTS

| WO | WO2012/065027 | 5/2012 |
|---|---|---|
| WO | WO 2012/135253 | 10/2012 |
| WO | WO 03/004626 | 1/2013 |

OTHER PUBLICATIONS

Payne, Using Immunomagnetic Technology and Other Means to Facilitate Stem Cell Homing, Medical Hypotheses 62: 718-720 (2004).

Zhao et al., Targeting Human CD34+ Hematopoietic Stem Cells With Anti-CD45 × Anti-Myosin Light-chain Bispecific Antibody Preserves Cardiac Function in Myocardial Infarction, J. Appl. Physiol. 104:1793-1800 (2008).

Abela et al., A New Method for Isolation of Cardiac Myocytes by Percutaneous Endomyocardial Biopsy, Catheterization and Cardiovascular Diagnosis, 1996, 37:227-230

Andersen et al., "Murine 'Cardiospheres' Are Not a Source of Stem Cells with Cardiomyogenic Potential," Stem Cells, 2009, vol. 27, No. 7, pp. 1571-1581.

Anversa et al., Primitive cells and tissue regeneration. Circ. Res. 92:579-92 (2003).

Ausma et al., "Dedifferentiation of atrial cardiomyocytes: from in vivo to in vitro", Cardiovascular Research, Jul. 2002, vol. 55(1), pp. 9-12.

Balser et al., Global parameter optimization for cardiac potassium channel gating models, Biophys. J., Mar. 1990, vol. 57, pp. 433-444.

Balser et al., Local Anesthetics as Effectors of Allosteric Gating, J. Clin. Invest., Dec. 1996, vol. 98(12), pp. 2874-2886.

Barile et al., Cardiac stem cells: isolation, expansion and experimental use for myocardial regeneration. Nat. Clin. Pract. Cardiovasc. Med. 4 Suppl 1: S9-S14 (2007).

Barile et al., Endogenous Cardiac Stem Cells. Prog. Cardiovas. Dis. 50(1):31-48 (2007).

Barr et al., Gene Therapy, Jan. 1994, vol. 1(1), pp. 51-58.

Barry et al., Differential Expression of Voltage-Gated K+ Channel Subunits in Adult Rat Heart, Circulation Research, 1995, vol. 77, pp. 361-369.

Barth et al., Lentiviral vectors bearing the cardiac promoter of the Na+—Ca2+ exchanger report cardiogenic differentiation in stem cells. Mol. Ther. 16(5):957-964 (2008).

Beltrami et al., "Adult cardiac stem cells are multipotent and support myocardial regeneration," Cell. vol. 114, No. 6, pp. 763-776 (2003).

Beltrami et al., Evidence that human cardiac myocytes divide after myocardial infarction. N. Engl. J. Med. 344: 1750-1757 (2001).

Benardeau et al., Primary culture of human atrial myocytes is associated with the appearance of structural and functional characteristics of immature myocardium. J. Mol. Cell Cardiol. 29: 1307-1320 (1997).

Bird et al., "The human adult cardiomyocyte phenotype", Cardiovascular Research, May 1, 2003, vol. 58(2), pp. 423-434.

Bosnali et al., "Generation of transducible versions of transcription factors Oct4 and Sox2," Biological Chemistry, Walter De Gruyter GmbH & Co., Berlin, DE, vol. 389(7), Jul. 1, 2008, pp. 851-861.

Chen et al., Vascular endothelial growth factor promotes cardiomyocyte differentiation of embryonic stem cells, Am J Physiol Heart Circ Physiol, Oct. 2006, vol. 291(4), pp. H1653-H1658.

Christmann et al., Biomaterials for the Treatment of Myocardial Infarction, J. Am. Coll. of Cardiol. (2006) vol. 48(5): 907-913.

De Pomerai et al., Influence of serum factors on the prevalence of "normal" and "foreign" differentiation pathways in cultures of chick embryo neuroretinal cells, J Embryol Exp Morphol., 1981, vol. 62, 291-308.

Deal et al., Molecular Physiology of Cardiac Potassium Channels, Physiological Reviews, Jan. 1996, vol. 76(1), pp. 49-67.

Dispersyn et al., Adult rabbit cardiomyocytes undergo hibernation-like dedifferentiation when co-cultured with cardiac fibroblasts. Cardiovasc. Res. 57: 230-240 (2001).

Dispersyn et al., Dissociation of cardiomyocyte apoptosis and dedifferentiation in infarct border zones. Eur. Heart J. 23:849-857 (2002).

Dixon et al., Quantitative Analysis of Potassium Channel mRNA Expression in Atrial and Ventricular Muscle of Rats, Circulation Research, 1994, vol. 75, pp. 252-260.

Dixon et al., Role of the Kv4.3 K+ Channel in Ventricular Muscle, Circulation Research, 1996, vol. 79, pp. 659-668.

Donahue et al., Ultrarapid, highly efficient viral gene transfer to the heart, Proc. Natl. Acad. Sci. USA 94:4664-4668 (1997).

Driesen et al., Structural adaptation in adult rabbit ventricular myocytes: influence of dynamic physical interaction with fibroblasts. Cell. Biochem. Biophys. 44: 119-128 (2006).

Driesen et al., Structural remodeling of cardiomyocytes in the border zone of infarcted rabbit heart. Mol. Cell. Biochem (2007), Mol Cell Biochem. Aug. 2007;302 (1-2) :225-32.

Engel et al., "p38 MAP kinase inhibition enables proliferation of adult mammalian cardiomyocytes", Genes & Dev., May 2005, vol. 19, No. 10, pp. 1175-1187.

Engel et al., FGF1/p38 MAP kinase inhibitor therapy induces cardiomyocyte mitosis, reduces scarring, and rescues function after myocardial infarction, Proc Nat Acad Sci (USA), Oct. 17, 2006, vol. 103(42), pp. 15546-15551.

Eschenhagen et al., Engineering Myocardial Tissue, Circ Res (2005) vol. 97:1220-1231.

Fiset et al., Shal-type channels contribute to the Ca2+-independent transient outward K+ current in rat ventricle, J. Physiology, 1997, vol. 500(1), pp. 51-64.

Gidh-Jain et al., Differential Expression of Voltage-Gated K+ Channel Genes in Left Ventricular Remodeled Myocardium After Experimental Myocardial Infarction, Circulation Research, 1996, vol. 79, pp. 669-675.

Glover et al., Reduction of infarct size and postschemic inflammation from ATL-146e, a highly selective adenosine A2A receptor agonist in reperfused canine myocardium, Amer J Physiol Heart Circ Physiol, Apr. 2005, vol. 288(4), pp. H1851-H1858.

Good et al., β-Amyloid Peptide Blocks the Fast-Inactivating K+ Current in Rat Hippocampal Neurons, Biophysical Journal, Jan. 1996, vol. 70, pp. 296-304.

Harvey, "Molecular Determinants of Cardiac Development and Congenital Disease," Mouse Development, Patterning, Morphogenesis, and Organogensis, Chapter 16, pp. 331-370, 2002.

Heng et al., "Incorporating protein transduction domains (PTD) within recombinant 'fusion' transcription factors. A novel strategy for directing stem cell differentiation?" Biomedicine and Pharmacotherapy, Elsevier, Paris, FR, vol. 59(3), Apr. 1, 2005, pp. 132-134.

Jackson et al., Regeneration of ischemic cardiac muscle and vascular endothelium by adult stem cells, J Clin Invest., 2001, vol. 107(11), pp. 1395-1402.

Kaab et al., Ionic mechanism of action potential prolongation in ventricular myocytes from dogs with pacing-induced heart failure. Circulation Research, vol. 78, No. 2, 262 (1996).

Kim et al., "Generation of human induced pluripotent stem cells by direct delivery of reprogramming proteins," Cell Stem Cell, Jun. 5, 2009, vol. 4(6), pp. 472-476.

Kuhn et al., Periostin induces proliferation of differentiated cardiomyocytes and promotes cardiac repair, Nature Medicine, Aug. 2007, vol. 13(8), pp. 962-969. Abstract only.

Kwon et al., "Cellular Manipulation of Human Embryonic Stem Cells by TAT-PDX1 Protein Transduction," Molecular Therapy, Academic Press, San Diego, CA, US, vol. 12(1), Jul. 1, 2005, pp. 28-32.

Lee et al., Cardiac gene transfer by intracoronary infusion of adenovirus vector-mediated reporter gene in the transplanted mouse heart. J. Thorac, and Cardio. Surg., 111:246 (1996).

Li et al., Molecular, Cellular, and Functional Phenotypes of Human Cardiac Stem Cells Dependent Upon Monolayer Versus Three-Dimensional Culture Conditions, Circulation Research, Dec. 4, 2009, vol. 105(12).

Li et al., Expansion of human cardiac stem cells in physiological oxygen improves cell production efficiency and potency for myocardial repair, Cardiovascular Research, Aug. 21, 2010.

Li et al., Stem Cell Technology: Epigenetics, Genomics, Proteomics, and Metabonomics, Stem Cells 2010; vol. 28, pp: 1178-1185.

Lyngbaek et al., Cardiac regeneration by resident stem and progenitor cells in the adult heart. Basic Res. Cardiol. 102: 101-114 (2007).

(56) References Cited

OTHER PUBLICATIONS

Maletic-Savatic et al., Differential Spatiotemporal Expression of K+ Channel Polypeptides in Rat Hippocampal Neurons Developing in situ and in vitro, Journal of Neuroscience, May 1995, vol. 15(5), pp. 3840-3851.
Marban, Big cells, little cells, stem cells: agents of cardiac plasticity. Circ Res. 100(4):445-6 (2007).
Marshall et al., The Jellyfish Green Fluorescent Protein: A New Tool for Studying Ion Channel Express and Function, Neuron, 1995, vol. 14, pp. 211-215.
McGann et al., Mammalian myotube dedifferentiation induced by newt regeneration extract. Proc. Natl. Acad. Sci. USA 98, 13699-704 (2001).
Messina et al., Isolation and Expansion of Adult Cardiac Stem Cells from Human and Murine Heart; Oct. 29, 2004; pp. 911-921; vol. 95; Circulation Research; Cellular Biology; American Heart Association.
Montessuit et al., "Regulation of glucose transporter expression in cardiac myocytes: p38 MAPK is a strong inducer of GLUT4", Cardiovascular Research, Oxford University Press, Oct. 1, 2004, vol. 64(1), pp. 94-104.
Montessuit et al., "Retinoic acids increase expression of GLUT4 in dedifferentiated and hypertrophied cardiac myocytes", Basic Research in Cardiology, Steinkopff-Verlag, DA, Jan. 1, 2006, vol. 101(1), pp. 27-35.
Nadal-Ginard et al, Myocyte death, growth, and regeneration in cardiac hypertrophy and failure. Circ. Res. 92(2):139-50 (2003).
Nadal-Ginard et al., A matter of life and death: cardiac myocyte apoptosis and regeneration. J. Clin. Invest. 111: 1457-9 (2003).
Odelberg, Inducing cellular dedifferentiation: a potential method for enhancing endogenous regeneration in mammals., Semin Cell Dev. Biol., 13(5):335-43 (2002).
Odelberg et al., Dedifferentiation of mammalian myotubes induced by msx1. Cell 103(7):1099-1109 (2000).
Oh et al., "Cardiac muscle plasticity in adult and embryo by heart-derived progenitor cells," Annals of the New York Academy of Sciences, vol. 1015, pp. 182-189 (2004).
Oh et al., Cardiac progenitor cells from adult myocardium: homing, differentiation, and fusion after infarction, Proc Natl Acad Sci USA, 2003, vol. 100(21), pp. 12313-12318.
Passier et al., Origin and use of embryonic and adult stem cells in differentiation and tissue repair. Cardiovasc. Res. 58(2):324-35 (2003).
Plotnikov et al., Biologial Pacemaker Implanted in Canine Left Bundle Branch Provides Ventricular Escape Rhythms that Have Physiologically Acceptable Rates, Circulation, Feb. 3, 2004, vol. 109, pp. 506-512.
Potapova et al., Enhanced recovery of mechanical function in the canine heart by seeding an extracellular matrix patch with mesenchymal stem cells committed to a cardiac lineage, Am. J. Phys. (2008) vol. 295:H2257-H2263.
Ribera, Homogeneous Development of Electrical Excitability via Heterogeneous Ion Channel Expression, Journal of Neuroscience, Feb. 1, 1996, vol. 16(3), pp. 1123-1130.
Risepro et al., Hand1 regulates cardiomyocyte proliferation versus differentiation in the developing heart, Development, Nov. 2006, vol. 133(22), pp. 4595-4606. Abstract only.
Rucker-Martin et al., Dedifferentiation of atrial myocytes during atrial fibrillation: role of fibroblast proliferation in vitro. Cardiovasc. Res. 55: 38-52 (2002).
Rudy, Diversity and Ubiquity of K Channels, Neuroscience, 1988, vol. 25(3), pp. 729-749.
Serodio et al., Cloning of a Novel Component of A-Type K+ Channels Operating at Subthreshold Potentials With Unique Expression in Heart and Brain, Journal of Neurophysiology, May 1996, vol. 75(5), pp. 2174-2179.
Smith et al., Regenerative potential of cardiosphere-derived cells expanded from percutanerous endomyocardial biopsy specimens, Circulation, Feb. 20, 2007, vol. 115(7), pp. 896-908.

Smith et al., Stem Cells in the heart: what's the buzz all about? Part 1: Preclinical considerations. Heart Rhythm 5(5):749-757(2008).
Smith et al., Stem Cells in the heart: what's the buzz all about? Part 2: Arrhythmic risks and clinical studies. Heart Rhythm 5(6):880-887 (2008).
Srivastava et al., Thymosin beta4 is cardioprotective after myocardial infarction, Ann NY Acad Sci, Sep. 2007, vol. 1112, pp. 161-170. Abstract only.
Sussman et al., Myocardial aging and senescence: where have the stem cells gone? Annu Rev. Physiol. 66:29-48 (2004).
Takahashi et al., "Induction of pluripotent stem cells from adult human fibroblasts by defined factors," Cell, Cell Press, Cambridge, MA, US, vol. 131(5), Nov. 30, 2007, pp. 861-872.
Tomita et al., Cardiac Neural Crest Cells Contribute to the Dorman Multipotent Stem Cell in the Mammalian Heart, Journal of Cell Biology, Sep. 26, 2005, vol. 170, No. 7, pp. 1135-1148.
Torella et al., Cardiac stem cell and myocyte aging, heart failure, and insulin-like growth factor-I overexpression. Circ. Res 94:514-24 (2004).
Torella et al., Resident human cardiac stem cells: role in cardiac cellular homeostasis and potential for myocardial regeneration. Nat. Clin. Pract. Cardiovasc. Med. 3 Suppl 1:S8-13 (2006).
Urbanek et al., Cardiac Stem Cells Possess Growth Factor Receptor Systems That After Activation Regenerate the Infarcted Myocardium, Improving Ventricular Function and Long-term Survival. Circ. Res. 97:663-673 (2005).
Urbanek et al., Intense myocyte formation from cardiac stem cells in human cardiac hypertrophy. Proc. Natl. Acad. Sci. USA 100(18):10440-5 (2003).
Urbanek et al., Myocardial regeneration by activation of multipotent cardiac stem cells in ischemic heart failure. Proc. Natl. Acad. Sci. USA 102(24):8692-7 (2005).
Ventura et al., Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts, JBC (2007) vol. 282(19):14243-14252.
Von Harsdorf, Can cardiomyocytes divide? Heart 86: 481-482 (2001).
Wagner, The state of the art in antisense research, Nature Medicine, Nov. 1995, vol. 1(11), pp. 1116-1118.
Walder et al., Up-regulation of neural stem cell markers suggests the occurrence of dedifferentiation in regenerating spinal cord. Dev. Genes Evol. 213: 625-630 (2003).
Wu et al., Cellular Therapy and Myocardial tissue engineering: the role of adult stem and progenitor cells. Eur. J. of Cardio-Thoracic Surg. 30:770-781 (2006).
Yu et al., "Induced pluripotent stem cell lines derived from human somatic cells," Science, American Association for the Advancement of Science, US, vol. 318(5858), Dec. 21, 2007, pp. 1917-1920.
Zammit et al., The skeletal muscle satellite cell: stem cell or son of stem cell? Differentiation 68: 193-204 (2001).
Zhang et al., "Do cardiac stem cells arise from cardiomyocyte dedifferentiation?", Circulation Research, Nov. 2006, vol. 99(11), p. 1278. Abstract only.
Zhou et al., "Generation of Induced Pluripotent Stem Cells Using Recombinant Proteins," Cell Stem Cell, Cell Press, US, vol. 4(5), May 1, 2009, pp. 381-384.
Web page titled: bioptome.com—Scholten Surgical Instructions; downloaded from <http://www.bioptome.com/pages.php?page=Products>, 2001, first date of publication unknown, printed on Nov. 1, 2005.
Abdel-Latif, A., et al., Adult bone marrow-derived cells for cardiac repair: a systematic review and meta-analysis. Arch Intern Med, 2007. 167(10): p. 989-97.
Alibini et al., A Rapid in Vitro Assay for Quantitating the Invasive Potential of Tumor Cells, Cancer Research, vol. 47:3239-3245 (1987).
Ames BN, Shigenaga MK, Hagen TM. Oxidants, antioxidants, and the degenerative diseases of aging. Proc Natl Acad Sci USA. 1993;90:7915-7922.
Barbash et al., "Systemic Delivery of Bone-Marrow-Derived Mesenchymal Stem Cells to the Infarcted Myocardium Feasibility,

(56) References Cited

OTHER PUBLICATIONS

Cell Migration, and Body Distribution," Circulation, Apr. 19, 2003, 108:863-868. American Heart Association, Inc.
Bearzi et al, Human Cardiac Stem Cells, PNAS, vol. 104(35): 14068-14073 (2007).
Bernanke, et al., Effects of Hyaluronic Acid on Cardioc Cushion Tissue Cells in Collagen Matrix Cultures, Texas Reports on Biology and Medicine, vol. 39:271-285 (1979).
Bergmann O, Bhardwaj RD, Bernard S, Zdunek S, Barnabe-Heider F, Walsh S, Zupicich J, Alkass K, Buchholz BA, Druid H, Jovinge S, Frisen J. Evidence for cardiomyocyte renewal in humans. Science. 2009;324:98-102.
Birks EJ, Tansley PD, Hardy J, George RS, Bowles CT, Burke M, Banner NR, Khaghani A, Yacoub MH. Left ventricular assist device and drug therapy for the reversal of heart failure. N. Engl J Med. 2006;355(18):1873-1884.
Bjelakovic G, Nikolova D, Gluud LL, Simonetti RG, Gluud C. Mortality in randomized trials of antioxidant supplements for primary and secondary prevention: systematic review and meta-analysis. JAMA. 2007;297:842-857.
Bredemeyer AL, Sharma GG, Huang CY, et al. ATM stabilizes DNA double-strand-break complexes during V(D)J recombination. Nature. 2006;442:466-470.
Cai et al., "Injectable glycosaminoglycan hydrogels for controlled release of human basic fibroblast growth factor," Biomaterials (2005), 26:6054-6067, Elsevier Ltd.
Chambers et al., Functional Expression Cloning of Nanog, a Pluripotency Sustaining Facot in Embryonic Stem Cells, Cell. May 30, 2003; 113(5):643-55.
Chen CS, Squire JA, Wells PG. Reduced tumorigenesis in p53 knockout mice exposed in utero to low-dose vitamin E. Cancer. 2009;115:1563-1575.
Cheng, et al., Functional performance of human caradiosphere-derived cells delivered in an in situ polymerizable hyaluronan-gelatin hydrogel, Biomaterials (2012). Doi10.1016/j.biomaterials. 2012.04.006.
Cheng K, Li Ts, Malliaras K, Davis DR, Zhang Y, Marban E. Magnetic targeting enhances engraftment and functional benefit of iron-labeled cardiosphere-derived cells in myocardial infarction. Circ Res. 2010;106:1570-1581.
Chimenti et al., "Relative Roles of Direct Regeneration Versus Paracrine Effects of Human Cardiosphere-Dervied Cells Transplanted Into Infarcted Mice," Circulation Research (2010) 106:971-980, American Heart Association, Inc.
Chimenti, I., et al., Abstract 3182: Paracrine Contribution versus Direct Regeneration in Cardiosphere-Derived Cell Therapy for Acute Myocardial Infarction. Circulation, 2009. 120(18_ MeetingAbstracts): p. S756-a-.
ClinicalTrials.gov, Identifier NCT00893360. CADUCEUS—CardioSphere-Derived aUtologous Stem CElls to Reverse ventricUlar dySfunction, 2009.
Conkright et al., A gene encoding an intestinal-enriched member of the Kruppel-like factor family exrpessein in intestinal epithelia cells, Nucleic Acids Res. 27 (5), 1263-1270 (1999).
Crisostomo et al., "Embryonic stem cells attenuate myocardial dysfunction and inflammation after surgical global ischemia via paracrine actions," Am J Physiol Heart Cirl Physiol (2008) 295:H1726-H1735.
Davis DR, Kizana E, Terrovitis J, Barth AS, Zhang, Y, Smith RR, Miake J, Marban E. Isolation and expansion of functionally competent cardiac progenitor cells directly from heart bippsies. J Mol Cell Cardiol. 2010;49:312-321.
Davis DR, Zhang Y, Smith RR, et al. Validation of the cardiosphere method to culture cardiac progenitor cells from myocardial tissue. PLoS One. 2009;4:e7195.
Davis, D.R., R.R. Smith, and E. Marban, Human Cardiospheres are a Source of Stem Cells with Cardiomyogenic Potential. Stem Cells, 2010. 28(5): p. 903-4.
Del Monte. et al. (2004) Proc Natl Acad Sci USA 101, 5622-7.
Djokic M, Le Beau MM, Swinnen LJ, et al. Post-transplant lymphoproliferative disorder subtypes correlate with different recurring chromosomal abnormalities. Genes Chromosomes Cancer. 2006;45:313-318.
Dong et al. (1991) Mol. Endocrinol. 5:1633.
Drakos SG, Kfoury AG, Hammond EH, Reid BB, Revelo MP, Rasmusson BY, Whitehead KJ, Salama ME, Selzman CH, Stehlik J, Clayson SE, Bristow MR, Renlund DG, Li DY. Impact of mechanical unloading on microvasculature and associated central remodeling features of the failing human heart. J Am Coll Cardiol. 2010;56(5):382-391.
Eguchi (2004) Med. Res. Rev. 24:182.
Elliot & O'Hare, 88 Cell 223-233 (1997).
Elliot & O'Hare, Intercellular Trafficking of VP22-GFP fusion proteins., Gene Therapy 6:149 (1999).
Falck J, Coates J, Jackson SP. Conserved modes of recruitment of ATM ATR and DNAPKcs to sites of DNA damage. Nature. 2005;434:605-611.
Fehrer C, Brunauer R, Laschober G, et al. Reduced oxygen tension attenuates differentiation capacity of human mesenchymal stem cells and prolongs their lifespan. Aging Cell. 2007;6:745-757.
Foreman J, Demidchik V, Bothwell JH, et al. Reactive oxygen species produced by NADPH oxidase regulate plant cell growth. Nature. 2003;422:442-446.
Frankel & Pabo, Cell 55:1189-93 (1988).
Freyman et al., "A quantitative, randomized study evaluating three methods of mesenchymal stem cell delivery following myocardial infarction," European Heart Journal, 2006, 27:1114-1122.
Furlani D, Li W, Pittermann E, et al. A transformed cell population derived from cultured mesenchymal stem cells has no functional effect after transplantation into the injured heart. Cell Transplant. 2009;18:319-331.
Galli, R., et al., Neural stem cells: an overview. Circ Res, 2003. 92(6): p. 598-608.
George RS, Sabharwal NK, Webb C, Yacoub MH, Bowles CT, Hedger M, Khaghani A, Birks EJ. Echocardiographic assessment of flow across continuous-flow ventricular assist devices at low speeds. J Heart Lung Transplant. 2010.
Gomez-Marquez et al. (1987) J. Immunol. 143:2740.
Gu, Bispecific Antibody Targeted Stem Cell Therapy for Myocardial Repair, University of California San Francisco and University of California Berkeley, 2008.
Gubbay et al., Nature, 6281:245-50 (1990).
Hacein-Bey-Abina et al., Science 2003; 302:415-9.
Hagege, A.A., et al., Skeletal myoblast transplantation in ischemic heart failure: long-term follow-up of the first phase I cohort of patients. Circulation, 2006. 114(1 Suppl): p. I108-13.
Hainsworth AH, Bhuiyan N, Green AR. The nitrone disodium 2,4-sulphophenyl-N-tert-butylnitrone is without cytoprotective effect on sodium nitroprusside-induced cell death in N1E-115 neuroblastoma cells in vitro. J Cereb Blood Flow Metab. 2008;28:24-28.
Haider, et al., Bone Marrow Stem Cell Transplantation for Cardiac Repair, Am. J. Phys. Heart Circ. Physiol., vol. 288:H2557-H2567 (2005).
Haj-Yahia S, Birks EJ, Dreyfus G, Khaghani A. Limited surgical approach for explanting the HeartMate II left ventricular assist device after myocardial recovery. J Thorac Cardiovasc Surg. 2008;135(2):453-454.
Heng, BC et al., "Incorporating Protein Transduction Domains (PTD) within Recombinant Fusion Transcription Factors. A Novel Strategy for Directing Stem Cell Differentiation?" Biomedicine and Pharmacotherapy, vol. 59(3):132-34 (2005).
Hochedlinger et al., Nature 441:1061-7(2006).
Ivanovic Z. Hypoxia in situ normoxia: The stem cell paradigm. J Cell Physiol. 2009;219:271-275.
Johnston PV, Sasano T, Mills K, Evers R, Lee ST, Smith RR, Lardo AC, Lai S, Steenbergen C, Gerstenblith G, Lange R, Marban E. Engraftment, differentiation, and functional benefits of autologous cardiosphere-derived cells in porcine ischemic cardiomyopathy. Circulation. 2009;120:1075-1083.
Jutkiewicz et al. (2006) Mol. Interven. 6:162.
Karlsson et al., Nature 344 (6269), 879-882 (1990).

(56) References Cited

OTHER PUBLICATIONS

Karoubi et al., "Single-cell hydrogel encapsulation for enhanced survivial of human marrow stromal cells," Biomaterials, 2009, 30:5445-5455, Elsevier Ltd.
Kutschka, et al., Collagen Matrices Enhance Survival of Transplanted Cardiomyoblasts and Contribute to Functional Improvement of Ischemic Rat Hearts, Circulation, vol. 114:I167-I173 (2006).
Kyrtatos et al., Magnetic Tagging Increases Delivery of Circulating Progenitors in Vascular Injury, J. Am. Coll. Cardiol. Intv. vol. 2:794-802 (2009).
Laflamme et al., Nat Biotechnology 25:1015-24 (2007).
Landazuri, N. and J.M. Le Doux, Complexation of retroviruses with charged polymers enhances gene transfer by increasing the rate that viruses are delivered to cells. J Gene Med, 2004. 6(12): p. 1304-19.
Lavon N, Narwani K, Golan-Lev T, et al. Derivation of euploid human embryonic stem cells from aneuploid embryos. Stem Cells. 2008;26:1874-1882.
Lee et al., Antibody Targeting of Stem Cells to Infarcted Myocardium, Stem Cells Translational and Clinical Research, vol. 25:712-717 (2007).
Leferovich et al. (2001) Proc. Natl. Acad. Sci. USA 98:9830.
Levenberg at al., Endothelial cells derived from human embryonic stem cells, PNAS, vol. 99(7): 4391-4396 (2002).
Levine M, Conry-Cantilena C, Wang Y, et al. Vitamin C pharmacokinetics in healthy volunteers: evidence for a recommended dietary allowance. Proc Natl Acad Sci USA. 1996;93:3704-3709.
Li, Z. et al., Imaging survival and function of transplanted cardiac resident stem cells. J Am Coll Cardiol, 2009. 53(14): p. 1229-40.
Liao et al., Enhanced efficiency of generating induced pluipotent stem (iPS) cells from human somatic cells by a combination of six transcription factors, Cell Research (2008), vol. 18: 600-603.
Lindsay, Curr. Op. Pharmacol. 2:587-94 (2002).
Lindsley et al. (2008) Curr. Cancer Drug Targets 8:7.
Lipinski, M.J., et al., Impact of intracoronary cell therapy on left ventricular function in the setting of acute myocardial infarction: a collaborative systematicreview and meta-analysis of controlled clinical trials. J Am Coll Cardiol, 2007. 50(18): p. 1761-7.
Lowrey et al., Proc Natl Acad Sci USA 105:2883-8 (2008).
Lum et al., The New Face of Bispecific Antibodies: Targeting Cancer and Much More, Exp. Hematol., vol. 24:1-6 (2006).
Maitra A, Arking DE, Shivapurkar N, et al. Genomic alterations in cultured human embryonic stem cells. Nat Genet. 2005;37:1099-1103.
Martens et al., "Percutaneous Cell Delivery Into the Heart Using Hydrogels Polymerizing in Situ," Cell Transplantation (2009), 18:297-304.
Mehmel HC, Stockins B, Ruffmann K, von Olshausen K, Schuler G, Kubler W. The linearity of the end-systolic pressure-volume relationship in man and its sensitivity for assessment of left ventricular function. Circulation. 1981;63:1216-1222.
Miller ER 3rd, Pastor-Barriuso R, Dalai D, et al. Meta-analysis: high-dosage vitamin E supplementation may increase all-cause mortality. Ann Intern Med. 2005;142:37-46.
Mitsui et al., Cell. May 30, 2003; 113(5):631-42.
Miyazono et al. (1988) J. Biol. Chem. 263:6407.
Moss et al., Dev. Biol. 258 (2), 432-442 (2003).
Moss, A. J., et al., Prophylactic implantation of a defibrillator in patients with myocardial infarction and reduced ejection fraction. N. Engl J Med, 2002. 346(12): p. 877-83.
Murata K, Iwata T, Nakashima S, Fox-Talbot K, Qian Z, Wilkes DS, Baldwin WM. C4d deposition and cellular infiltrates as markers of acute rejection in rat models of orthotopic lung transplantation. Transplantation. 2008;86:123-129.
Nakagawa et al., Nat Biotechnol 26:101-6 (2008).
Nelson et al., Stem Cells 26:1464-73 (2008).
Nelson, T.J., et al., Repair of acute myocardial infarction by human stemness factors induced pluripotent stem cells. Circulation, 2009. 120(5): p. 408-16.
Niethammer P, Grabher C, Look AT, Mitchison TJ. A tissue-scale gradient of hydrogen peroxide mediates rapid wound detection in zebrafish. Nature. 2009;459:996-999.
Noguchi et al., Protein Transduction Technology: A Novel Therepeautic Perspective, Acta Medica Okayama (2005) vol. 60(1): 1-11.
Nussbaum, J., et al., Transplantation of undifferentiated murine embryonic stem cells in the heart: teratoma formation and immune response. Faseb J, 2007. 21(7):p. 1345-57.
Okita et al., Generation of Mouse Induced Pluripotent Stem Cells Without Viral Vectors, (2008), Science Express, 322:949-53 (Oct. 9, 2008).
Owusu-Ansah E, Banerjee U. Reactive oxygen species prime *Drosophila haematopoietic* progenitors for differentiation. Nature. 2009;461:537-541.
Park et al., Nature 451:141-6 (2008).
Passier et al. (2008) Nature 453:322.
Payne, Using Immunomagnetic Technologi and Other Means to Facilitate Stem Cell Homing, Medical Hypotheses, vol. 62:718-720 (2004).
Peterson, E.D., L.J. Shaw, and R.M. Califf, Risk stratification after myocardial infarction. Ann Intern Med, 1997. 126(7): p. 561-82.
Physicians ATSACoC. ATS/ACCP Statement on Cardiopulmonary Exercise Testing. American Journal of Respiratory and Critical CareMedicine. 2003;167:211-277.
Prunier et al. Am J Physiol Heart Circ Physiol (2006).
Qin K, Zhao L, Ash RD, McDonough WF, Zhao RY. ATM-mediated transcriptional elevation of prion in response to copper-induced oxidative stress. J Biol Chem. 2009;284:4582-4593.
Quevedo, H.C., et al., Allogeneic mesenchymal stem cells restore cardiac function in chronic ischemic cardiomyopathy via trilineage differentiating capacity. Proc Natl Acad Sci U S A, 2009. 106(33): p. 14022-7.
Rossi DJ, Bryder D, Seita J, et al. Deficiencies in DNA damage repair limit the function of haematopoietic stem cells with age. Nature. 2007;447:725-729.
Rotwein et al. (1986) J. Biol. Chem. 261:4828).
Rubio D, Garcia-Castro J, Martin MC, et al. Spontaneous human adult stem cell transformation. Cancer Res. 2005;65:3035-3039.
Sempere et al., Genome Biol. 5 (3), R13 (2004).
Sesso HD, Buring JE, Christen WG, et al. Vitamins E and C in the prevention of cardiovascular disease in men: the Physicians' Health Study II randomized controlled trial. JAMA. 2008;300:2123-2133.
Sharkey et al. (1995) Biol. Reprod. 53:974).
Shen et al. (1988) Proc. Natl. Acad. Sci. USA 85:1947.
Shu et al., Disulfide-crosslinked hyaluronon-gelatin hydrogel films: a covalent mimic of the extracellular matrix for in vitro cell growth, Biomaterials, vol. 24:3825-3834 (2003).
Simpson et al. (2007) Stem Cells 25:2350).
Singh U, Otvos J, Dasgupta A, et al. High-dose alpha-tocopherol therapy does not affect HDL subfractions in patients with coronary artery disease on statin therapy. Clin Chem. 2007;53:525-528.
Slaughter MS, Pagani FD, Rogers JG, Miller LW, Sun B, Russell SD, Starling RC, Chen L, Boyle AJ, Chillcott S, Adamson RM, Blood MS, Camacho MT, Idrissi KA, Petty M, Sobieski M, Wright S, Myers TJ, Farrar DJ. Clinical management of continuous-flow left ventricular assist devices in advanced heart failure. J Heart Lung Transplant. 2010;29(4 Suppl):S1-39.
Smart et al., De novocardiomyocytes from within the activated adult heart after injury. Nature. (2011) pp. 1-7.
Stewart S, Winters GL, Fishbein MC, et al. Revision of the 1990 working formulation for the standardization of nomenclature in the diagnosis of heart rejection, J Heart Lung Transplant. 2005;24:1710-1720.
Takahashi et al., Induction of Pluripotent Stem Cells from Adult Human Fibroblasts by Defined Factors (2007) Cell, vol. 131:1-12.
Takahashi et al., Induction of Pluripotent Stem Cells from Fibroblast Cultures, Nature Protocols, vol. 2 No. 12, 3081-9 (2007).
Takeda et al., Nucleic Acids Res. 20 (17), 4613-4620 (1992).
Takehara et al., J. Am. Coll. Cardiol. (2008) 52:1858-65.
Takeshita et al. (1993) Biochem. J. 294:271.
Ten Dijke et al. (1988) Proc. Natl. Acad. Sci. USA 85:4715).

(56) References Cited

OTHER PUBLICATIONS

Terrovitis J, Lautamaki R, Bonios M, Fox J, Engles JM, Yu J, Leppo MK, Pomper MG, Wahl RL, Seidel J, Tsui BM, Bengel FM, Abraham MR, Marban E. Noninvasive quantification and optimization of acute cell retention by in vivo positron emission tomography after intramyocardial cardiac-derived stem cell delivery. J Am Coll Cardiol. 2009;54:1619-1626.

Terrovitis, J.V., R.R. Smith, and E. Marban, Assessment and optimization of cell engraftment after transplantation into the heart. Circ Res. 106(3): p. 479-94, 2010.

Trevethick et al., (2008) Br J Pharmacol. 155:463.

Tsagalou EP, Anastasiou-Nana M, Agapitos E, Gika A, Drakos SG, Terrovitis JV, Ntalianis A, Nanas JN. Depressed coronary flow reserve is associated with decreased myocardial capillary density in patients with heart failure due to idiopathic dilated cardiomyopathy. J Am Coll Cardiol.2008;52(17):1391-1398.

Uemura et al., "Bone marrow Stem Cells Prevent Left Ventricular Remodeling of Ischemic Heart Through Paracrine Signaling," Circulation Research, 2006, 98:1414-1421, American Heart Association.

Ueno S. et al., Biphasic role for WNT/beta-catenin signaling in cardiac specification in zebrafish and embyonic stem cells. PNAS 104L9685 (2007).

van der Geest, R, Quantification in Cardiac MRI, Journal of Magnetic Resonance Imaging, 10:602-608(1999).

van Gent DC, Hoeijmakers JH, Kanaar R. Chromosomal stability and the DNA doublestranded break connection. Nat Rev Genet. 2001;2:196-206.

Vela et al. (2008) Cardiovasc. Pathol. 17:1.

Wang et al. (1994) Endocrinol. 134:1416.

Wang F, Thirumangalathu S, Loeken MR. Establishment of new mouse embryonic stem cell lines is improved by physiological glucose and oxygen. Cloning Stem Cells. 2006;8:108-116.

Web Page titled; Culture Media Database—EGM-2 (Endothelial Growth Medium 2)—ID 63; downloaded from <http://bio.Ionza.com/3018.html#ext-comp-1003:tab_63:change>; printed on Jan. 14, 2013.

Wernig el al., Cell Stem Cell 2: 10-2 (2008).

Wilmut et al., Nature 385:810-3 (1997).

Wilson KD, Huang M, Wu JC. Bioluminescence reporter gene imaging of human embryonic stem cell survival, proliferation, and fate. Methods Mol Biol. 2009; 574:87-103.

Yamada Y, Sekine Y, Yoshida S, Yasufuku K, Petrache I, Benson HL, Brand DD, Yoshino I, Wilkes DS. Type v collagen-induced oral tolerance plus low-dose cyclosporine prevents rejection of mhc class i and ii incompatible lung allografts. J Immunology. 2009;1:237-246 8.

Zhao et al., Targeting Human CD34+ Hematopoietic Stem Cells With Anti-CD45 × Anti-Myosin Light-chain Bispecific Antibody Preserves Cardiac Function in Myocardial Infarction, J. Appl. Phsyiol., vol. 104:1793-1800 (2008).

Chen CS, Wells PG. Enhanced tumorigenesis in p53 knockout mice exposed in utero to high-dose vitamin E. Carcinogenesis. 2006;27:1358-1368.

Cheng et al., Transplantation of platelet gel spike with cardiosphere-derived cells boosts structural and functional benefits relative to gel transplantation alone in rats with myocardial infarction, Biomaterials, vol. 33:2872-2879 (2012).

Davis DR, Kizana E, Terrovitis J, Barth AS, Zhang Y, Smith RR, Miake J, Marban E. Isolation and expansion of functionally-competent cardiac progenitor cells directly from heart biopsies. J Mol Cell Cardiol. 2010;49:312-321.

Deregibus, et al., Endotheial progenitor cell-derived microvesicles activate an angiogenic program in endothelial cells by a horizontal transfer of mRNA, Blood, 2007, 2440-2448.

Eppenberger-Eberhardt et al., Reexpression of alpha-Smooth Muscle Acting Isoform in Culture Adult Rat Cardiomyocytes, Dev Biol. Jun. 1990; 139 (2) :269-78.

Gatti et al., Microvesicles derived from human adult mesenchymal stem cells protect against ischaemia reperfusion-induced acute and chronic kidney injury, Nephrol. Dial. Transplant., vol. 26(5):1474-1483 (2011).

Hergenreider et al., Atheroprotective communication between endothelial cells and smooth muscle cells through miRNAs, Nat. Cell Biol., vol. 14(3):249-256 (2012).

Herrera et al., Human liver stem cell-derived microvesicles accelerate hepatic regeneration in hepatectomized rats, J. Cell. Mol. Med., vol. 14(6B):1605-1618 (2010).

Hierlihy et al., The Post-natal Heart Contains a Myocardial Stem Cell Population, FEBS Letters, vol. 530(1-3):239-243 (2002).

Hullinger et al., Inhibition of miR-15 protects against cardiac ischemic injury, Circ. Res. vol. 110(1):71-81 (2012).

Jayawardena et al., MicroRNA-mediated in vitro and in vivo direct reprogramming of cardiac fibroblasts to cardiomyocytes, Circ. Res. vol. 110(11)L1465-73 (2012).

Leor, et al., Transplantation of Fetal Myocardial Tissue Into the Infarcted Myocardium of Rat, Circulation, vol. 94(9): II-332 (1996).

Mangi et al., "Mesenchymal stem cells modified with Akt prevent remodeling and restore performance of infarcted hearts," Nature Medicine, Sep. 2003, 9(9):1195-1201, Nature Publishing Group.

Nakasa et al., Acceleration of muscle regeneration by local injection of muscle-specific microRNAs in rat skeletal muscle injury model, J. Cell. Mol. Med., vol. 14(10): 2495-2505 (2010).

Pike et al., "Herparin-regulated release of growth factors in vitro and angiogenic response in vivo to implanted hyaluronan hydrogels containing VEGF and bFGF," Biomaterials, (2006) 27:5242-5241, Elsevier Ltd.

Prestwich, et al., The translational imperative: Making Cell Therapy Simple and Effective, Acta Biomaterialia, vol. 8: 4200-4207 (2012).

Shimizu et al., Fabrication of Pulsatile Cardiac Tissue Grafts Using a Novel 3-D Cell Sheet Manipulation Techniques and Temperature-Responsive Cell Culture Surfaces, Circ. Res., vol. 90(3);e40 (2002).

Singh J. Enabling Technologies for Homing and Engraftment of Cells for Therapeutic Applications. J Am Coll Cardiol Intv. 2009;2(8):803-804.

Takahashi et al., Nat Protoc 2: 3081-9 (2007).

Van Winkle et al, "Cardiogel: A Biosynthetic Extracellular Matrix for Cardiomyocyte Culture," in Vitro Dev. Biol.—Animal, vol. 21, 1996, pp. 478-485.

Vela, et al., Quest for the cardiovascular holy grail: mammalian myocardial regeneration, Cardiovasc. Pathol. 17:1-5 (2008).

Yu et al., miR-221 and miR-222 promote Schwann cell proliferation and migration by targeting LASS2 after sciatic nerve injury, J. Cell Sci., vol. 125(11)"2675-2683 (2012).

Zhou et al., Down-Regulation of microRNA-26a Promotes Mouse Hepatocyte Proliferation during Liver Regeneration, PLoS ONE, vol. 7(4):e33577 (2012).

Assmus, et al., Transplantation of Progenitor Cells and Regeneration Enhancement in Acute Myocardial Infarction (TOPCARE-AMI), Circulation, vol. 106: 3009-3017 (2002).

Cho et al., Secondary Sphere Formation Enhances the Functionality of Cardiac Progenitor Cells, Mol. Ther., vol. 20(9):1750-1766 (2012).

Li, T-S et al., Direct comparison of different stem cell types and subpopulations reveals superior paracrine potency and myocardial repair efficacy with cardiosphere-derived cells, J. Am. Coll. Cardiol., vol. 59(10):942-953 (2012).

Lin et al., Accelerated Growth and Prolonged Lifespan of Adipose Tissue-Derived Human Mesenchymal Stem Cells in a Medium Using Reduced Calcium and Antioxidants, Stem Cells and Development, vol. 14:92-102 (2005).

Naka et al., Regulation of Reactive Oxygen Species and Genomic Stability in Hematopoietic Stem Cells, Antiox. Redox Signaling, vol. 10)11):1883-1884 (2008).

(56) References Cited

OTHER PUBLICATIONS

Puceat, M., Role of Rac-GTPase and Reactive Oxygen Species in Cardiac Differentiation of Stem Cell., Antiox. Redox. Signaling, vol. 7(11-12)"1435-1439 (2005).

Vrijsen, et al., Cardiomyocyte progenitor cell-derived exosomes stimulate migration of endothelial cells, J. Cell. Mol. Med., vol. 14(5):1064-1070 (2010).

Yau et al., Beneficial Effect of Autologous Cell Transplantation on Infarcted Heart Function: Comparison Between Bone Marrow Stromal Cells and Heart Cells, Annals of Thoracic Surg, vol. 75(1):169 (2003).

Zha, et al., Complementary Function of ATM and H2AX in Development and Suppression of Genomic Instability, PNAS, vol. 105(27):9302-9306 (2008).

\* cited by examiner

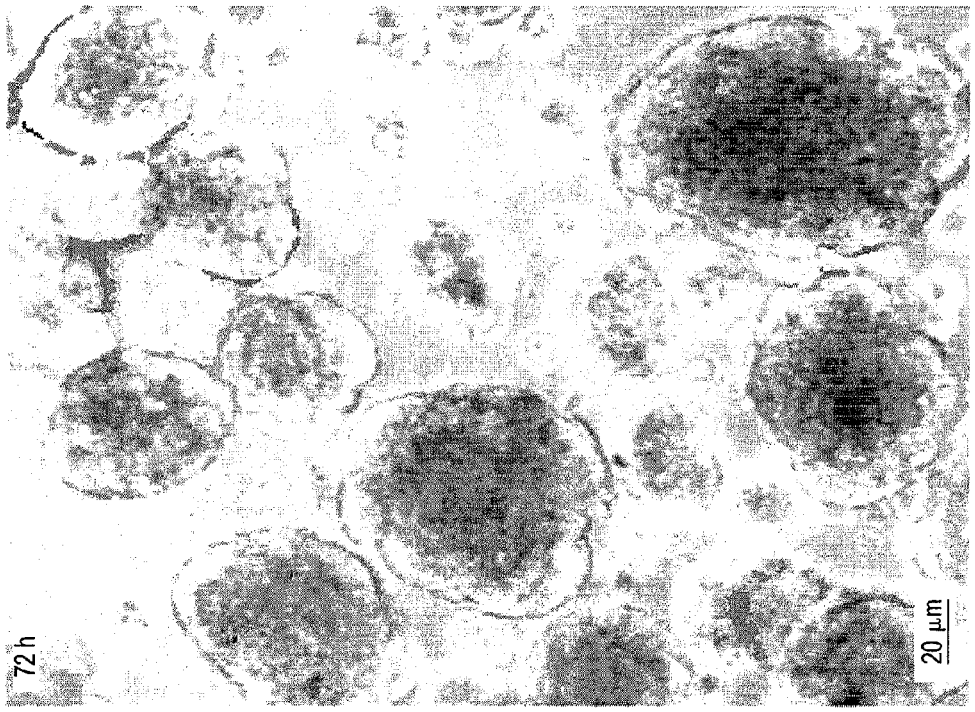
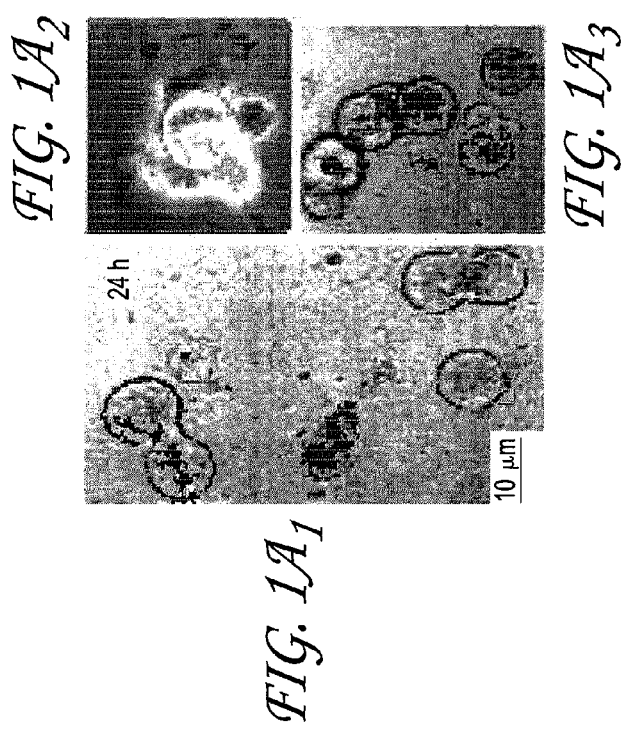
FIG. 1A₁  FIG. 1A₂  FIG. 1A₃  FIG. 1A₄
Human cardiospheres in culture

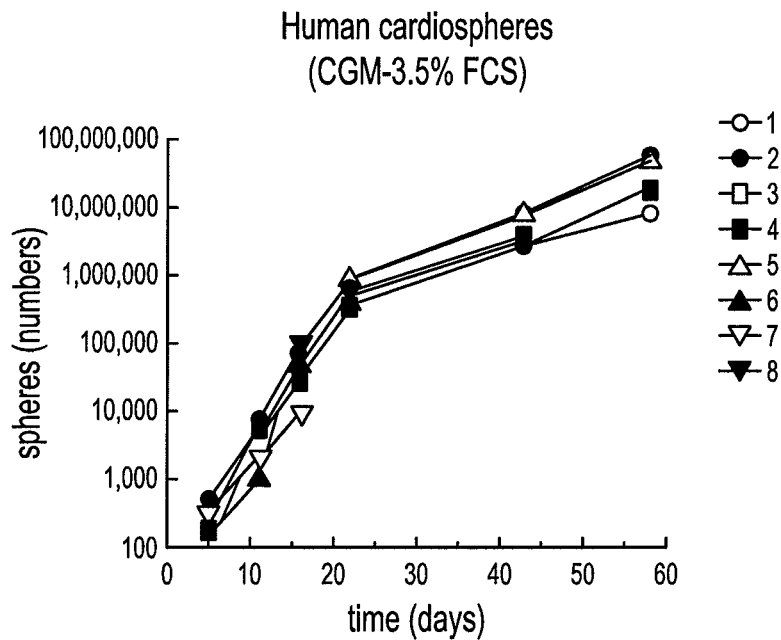
FIG. 1B₁
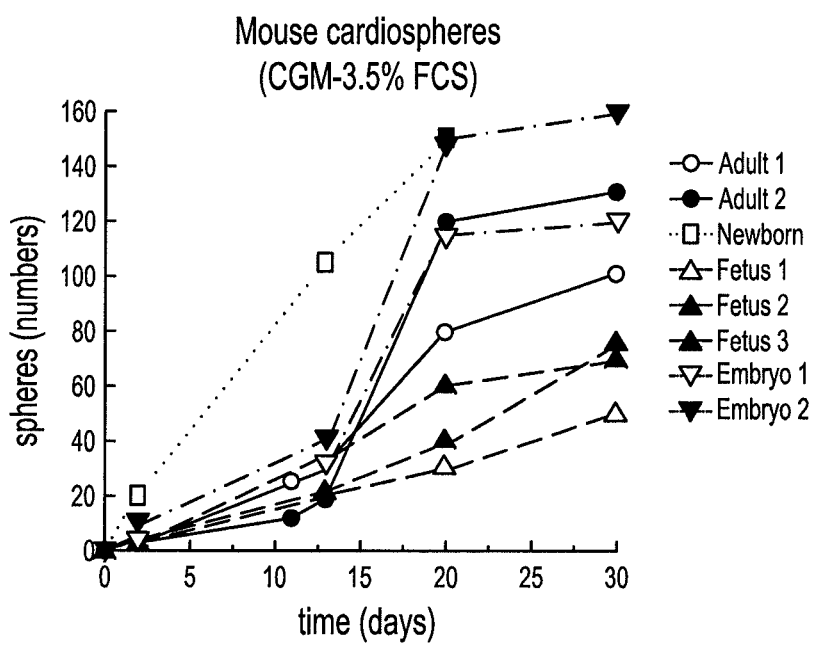
FIG. 1B₂

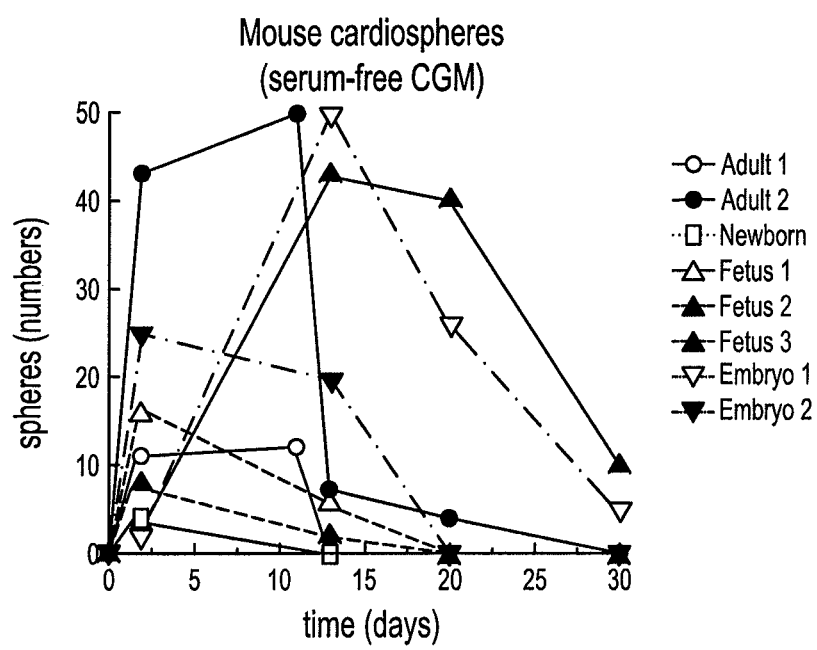
FIG. 1B₃

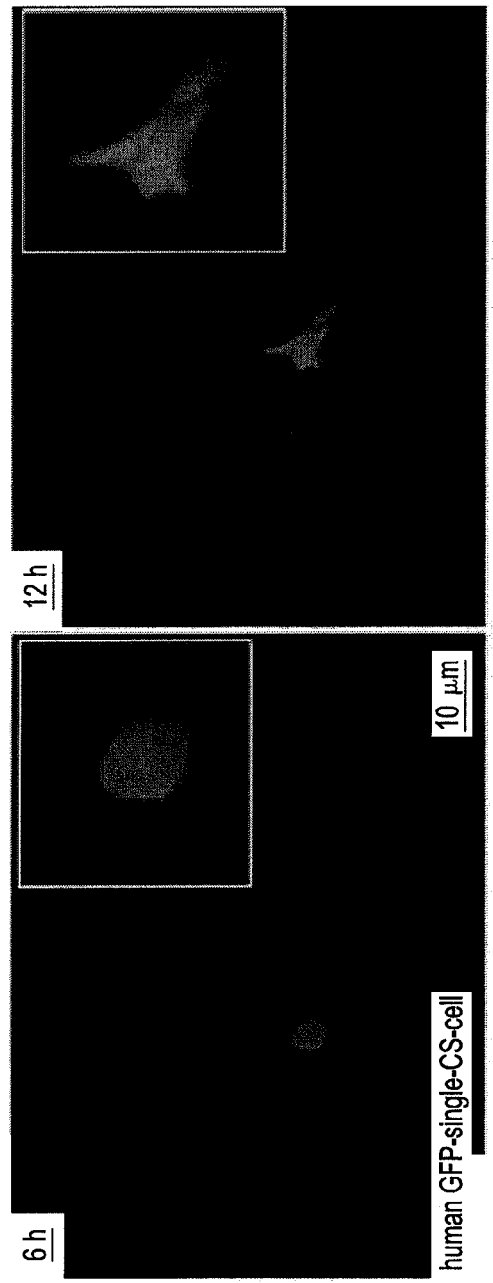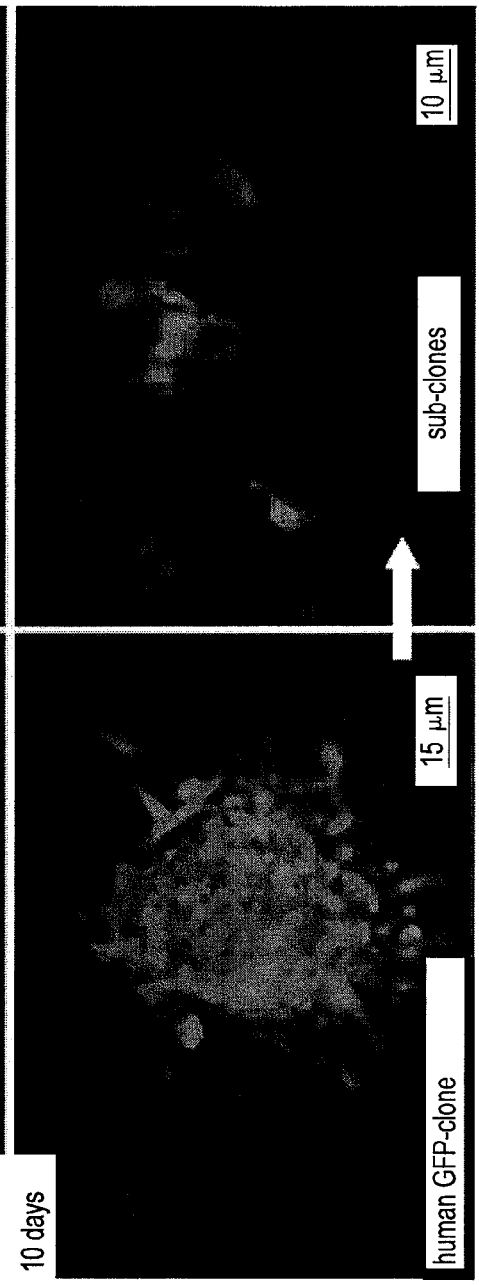

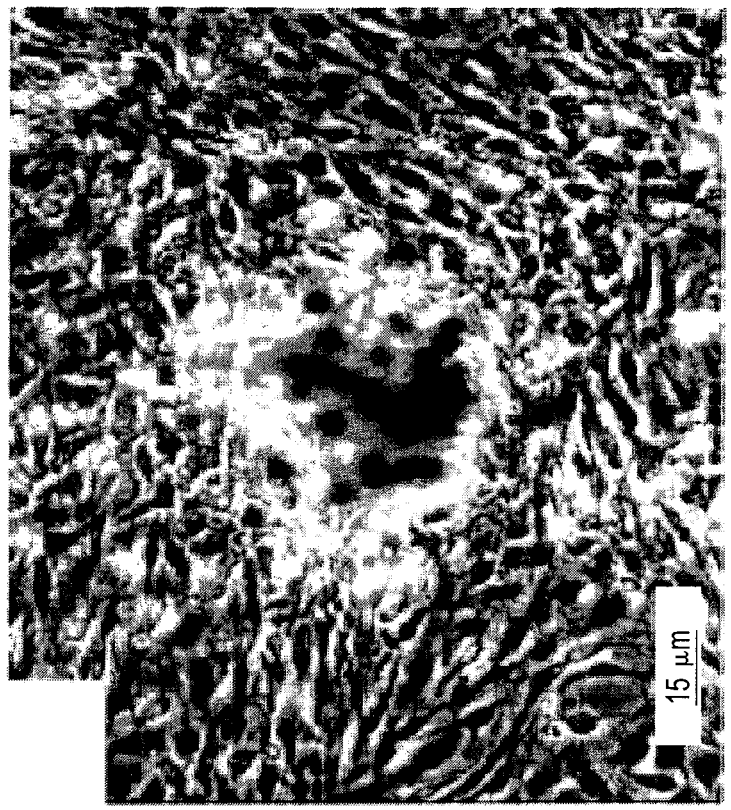
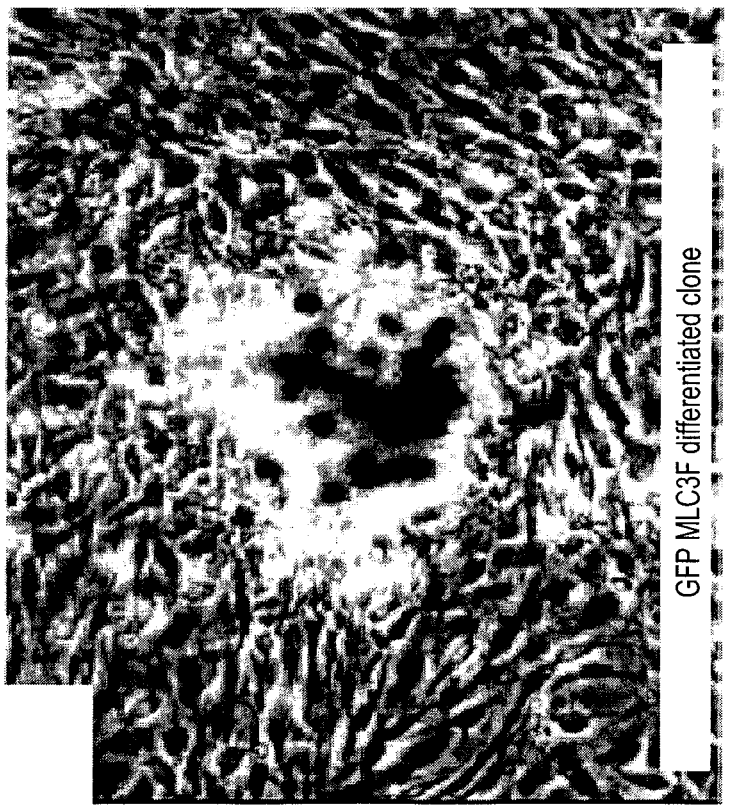
FIG. 1D₁  FIG. 1D₂

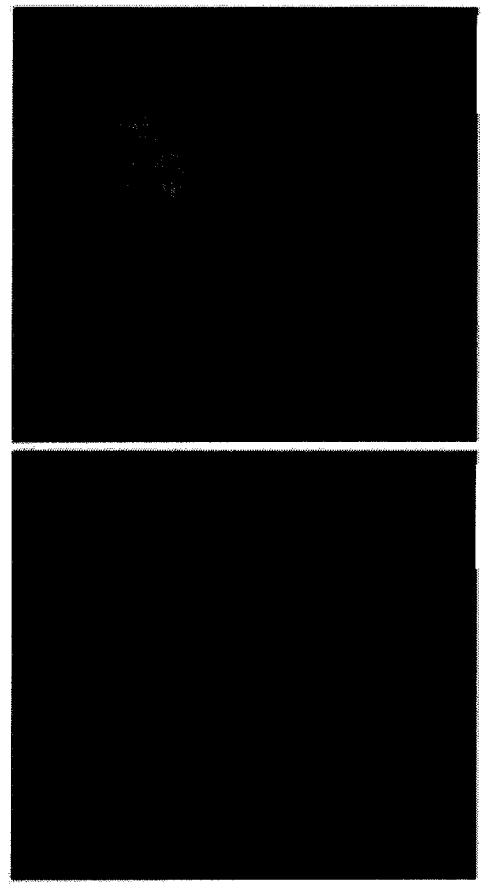
FIG. 2A₃
FIG. 2A₂
FIG. 2A₅
FIG. 2A₄
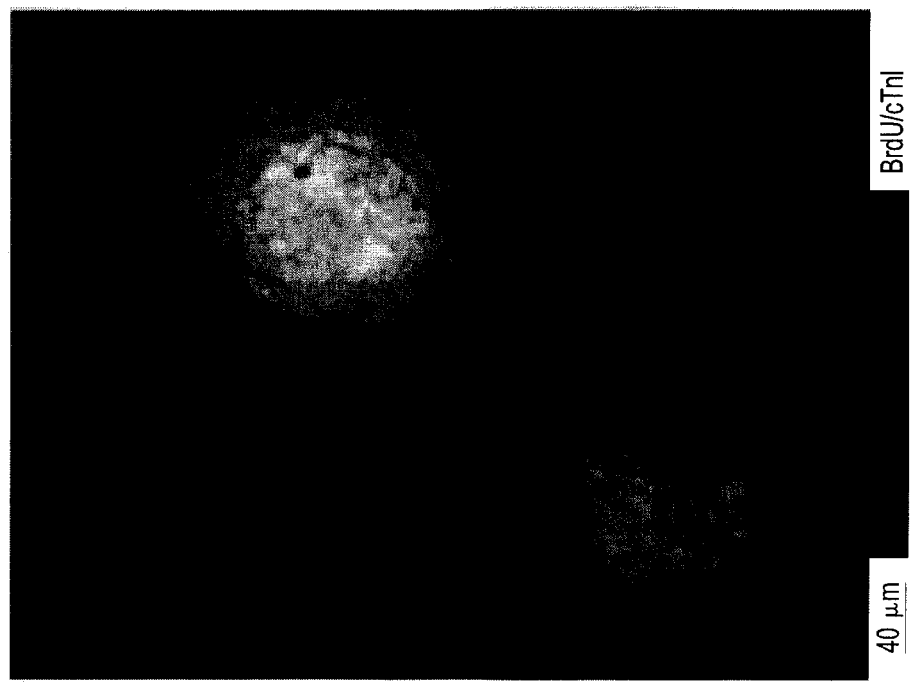
FIG. 2A₁

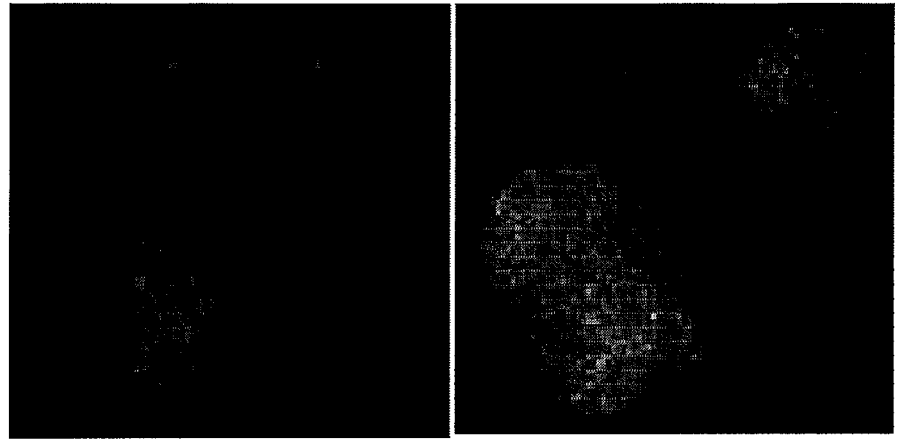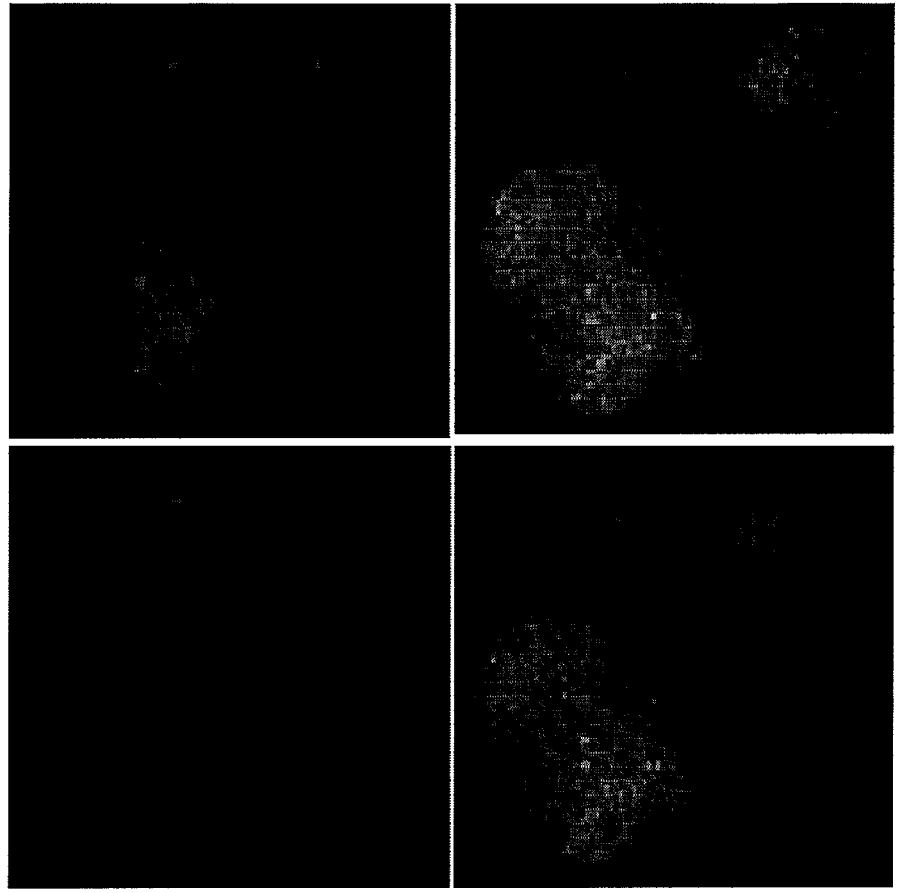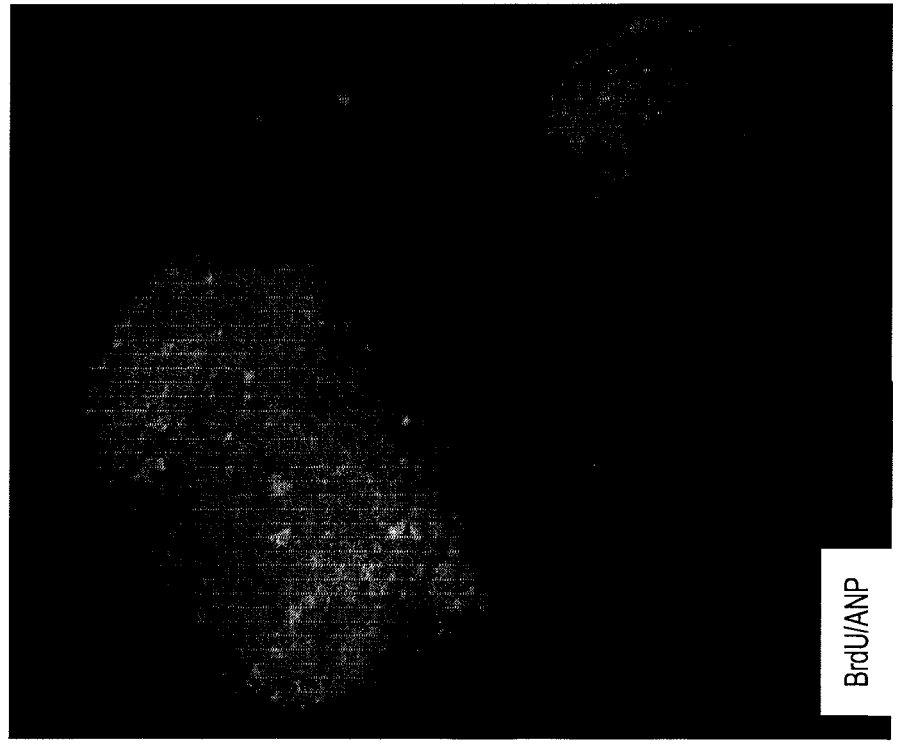

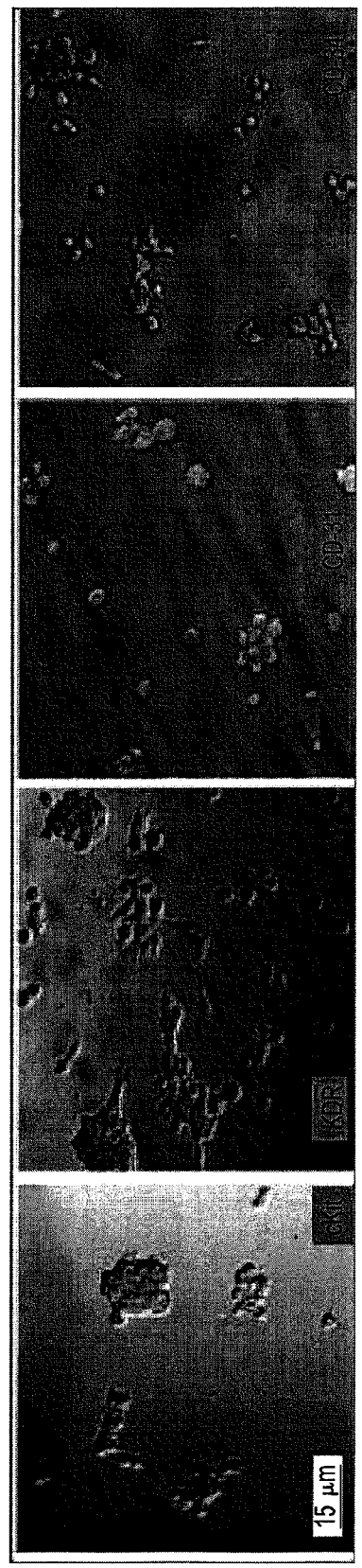
FIG. 2B₁  FIG. 2B₂  FIG. 2B₃  FIG. 2B₄

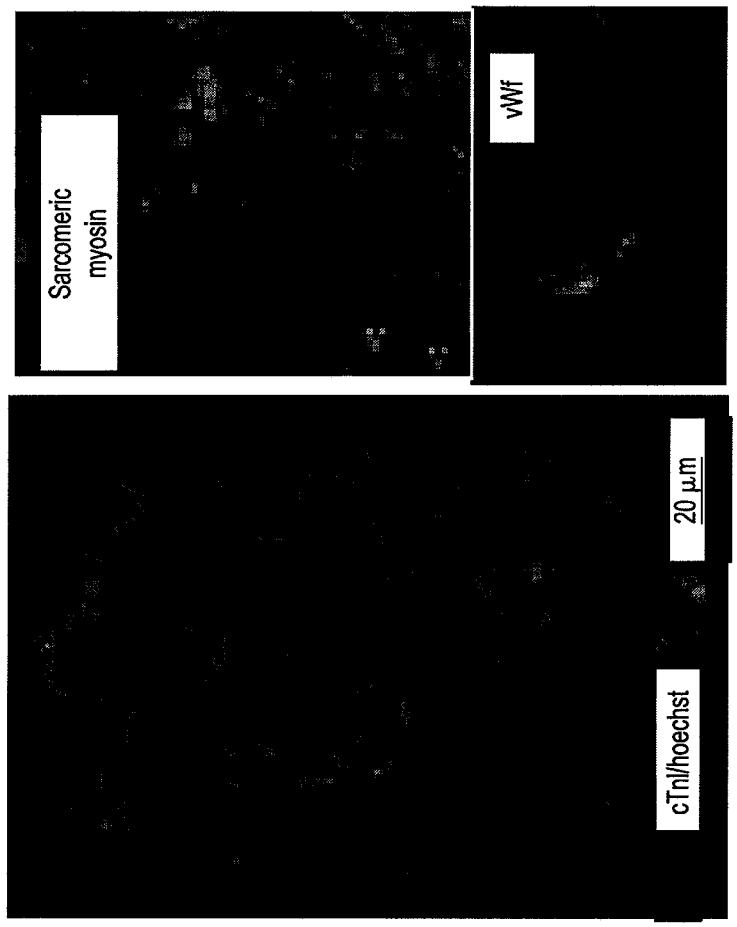

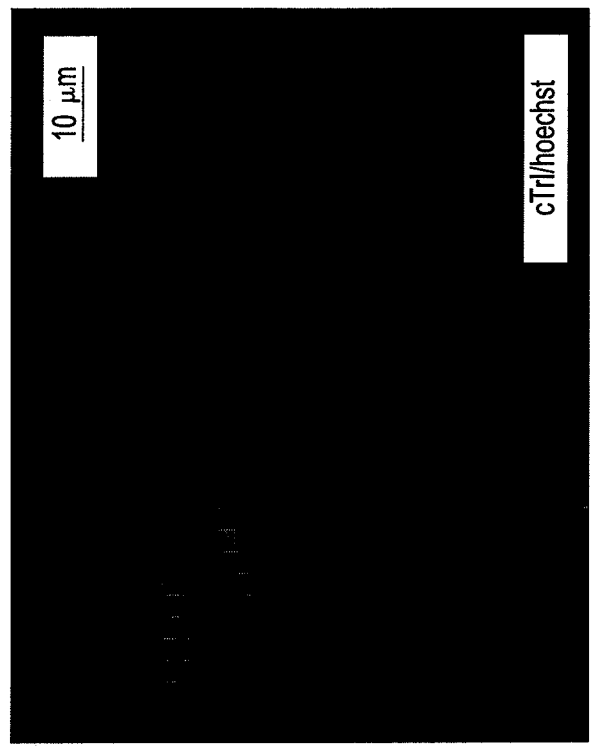
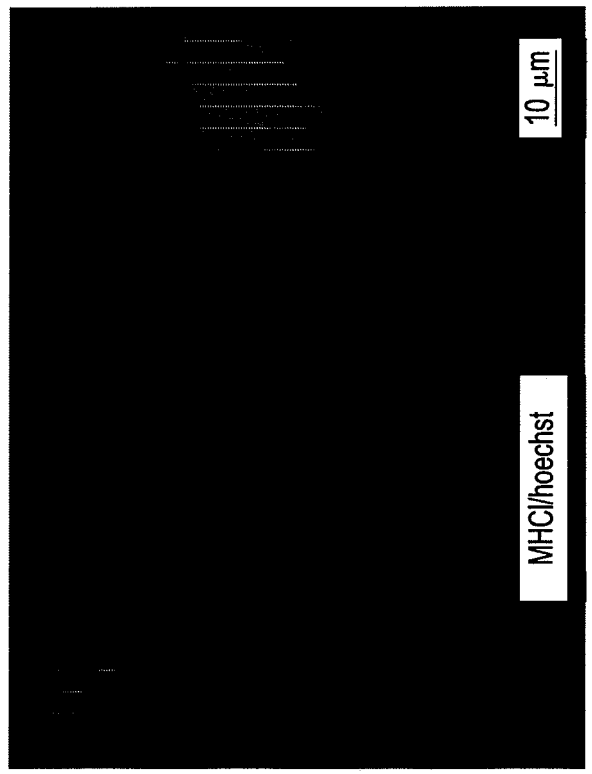
FIG. 2D₁
FIG. 2D₂

*FIG. 2E₁*  *FIG. 2E₂*  *FIG. 2E₃*
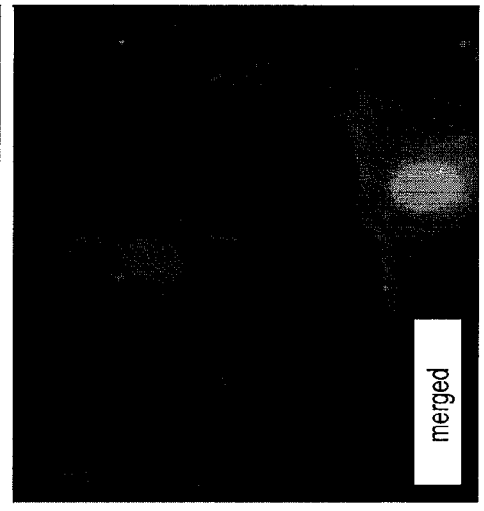
*FIG. 2F₁*  *FIG. 2F₂*  *FIG. 2F₃*

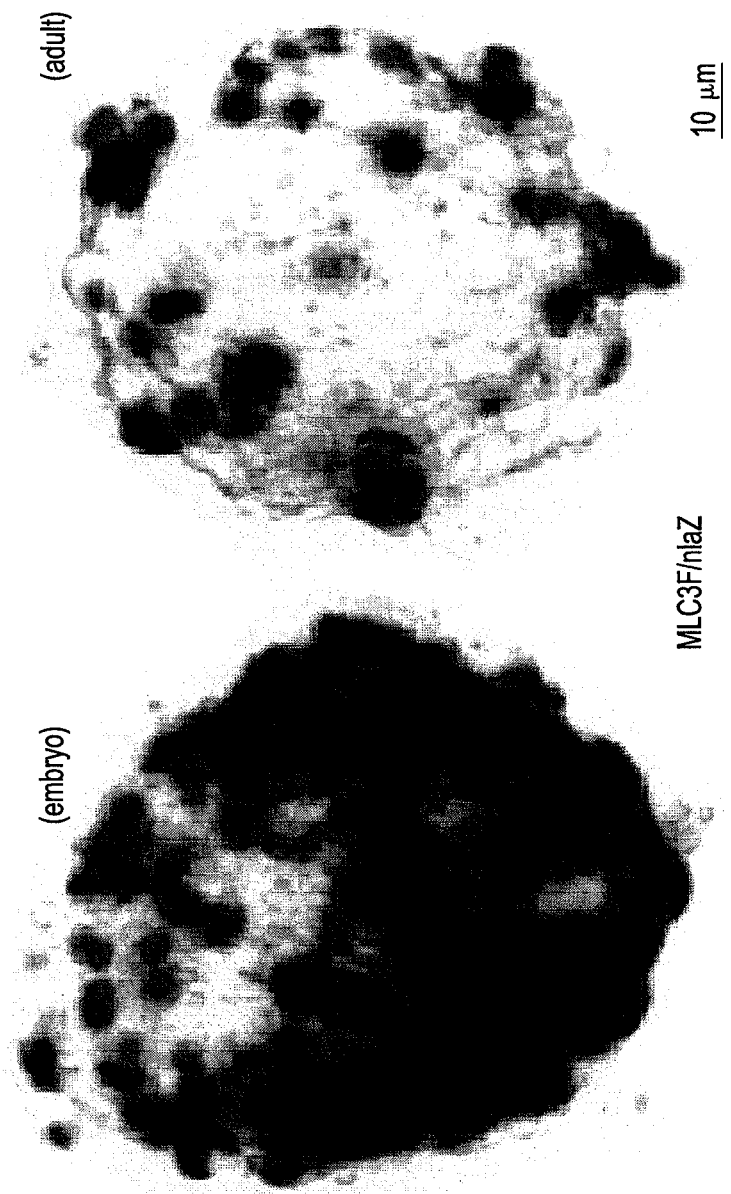

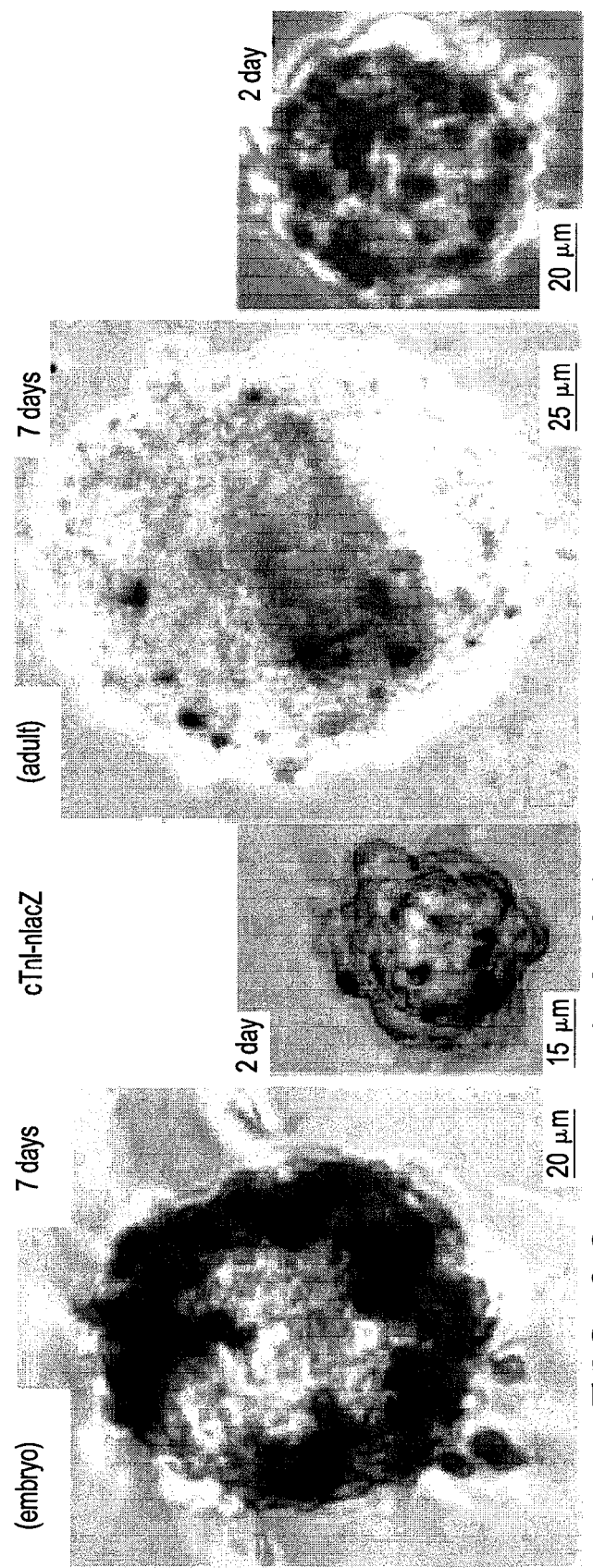
FIG. 2G₃  FIG. 2G₄  FIG. 2G₅  FIG. 2G₆

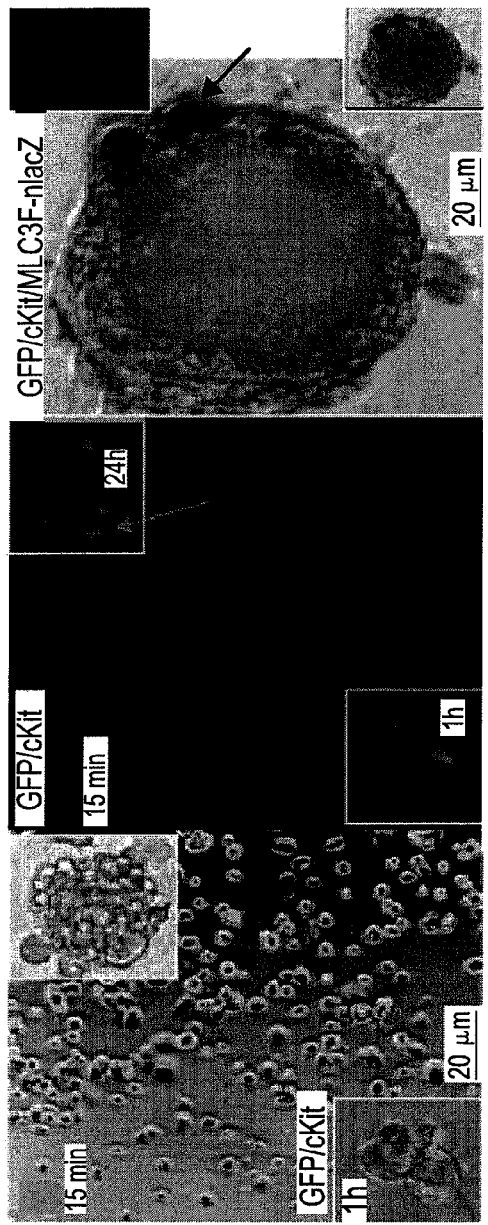

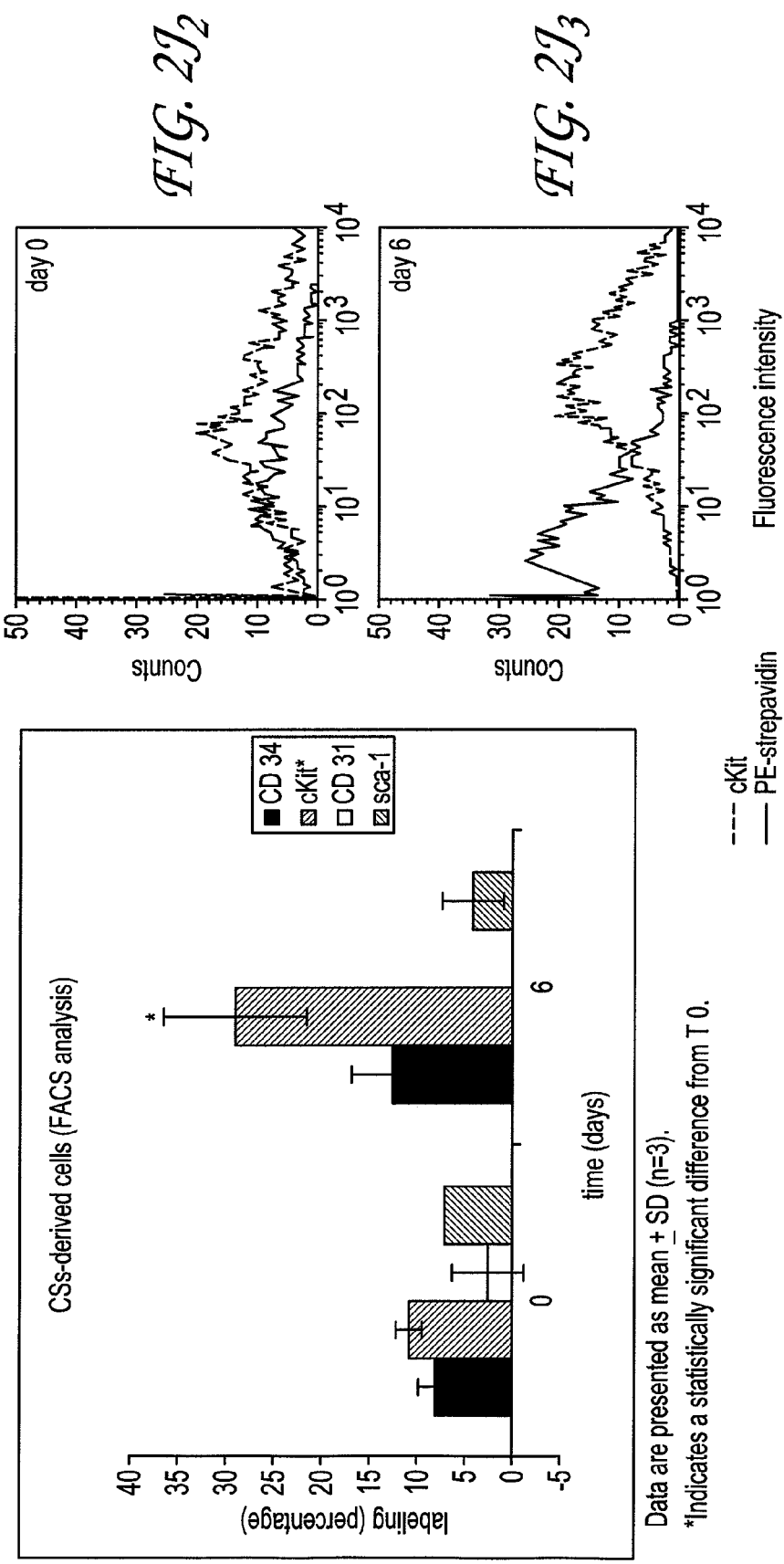

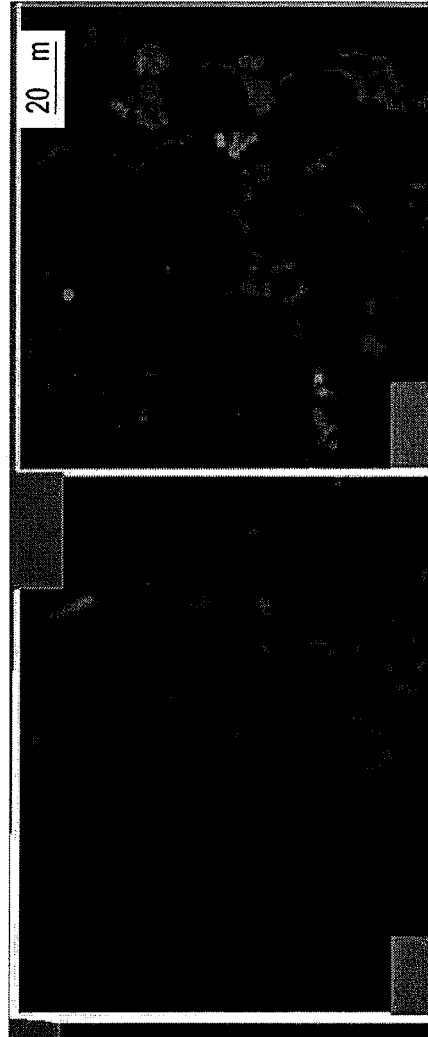
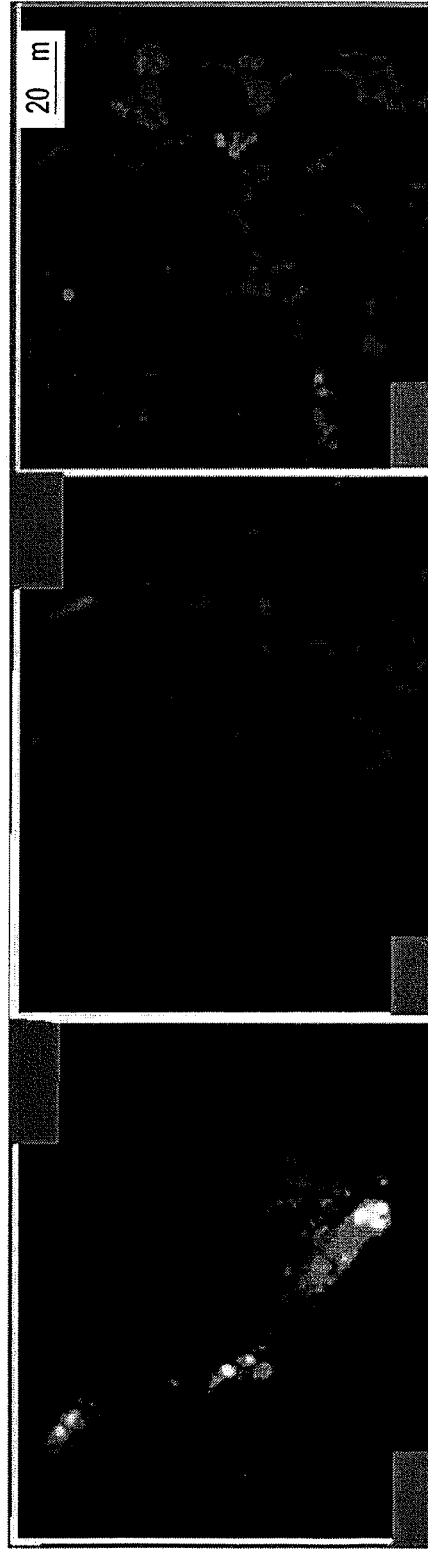
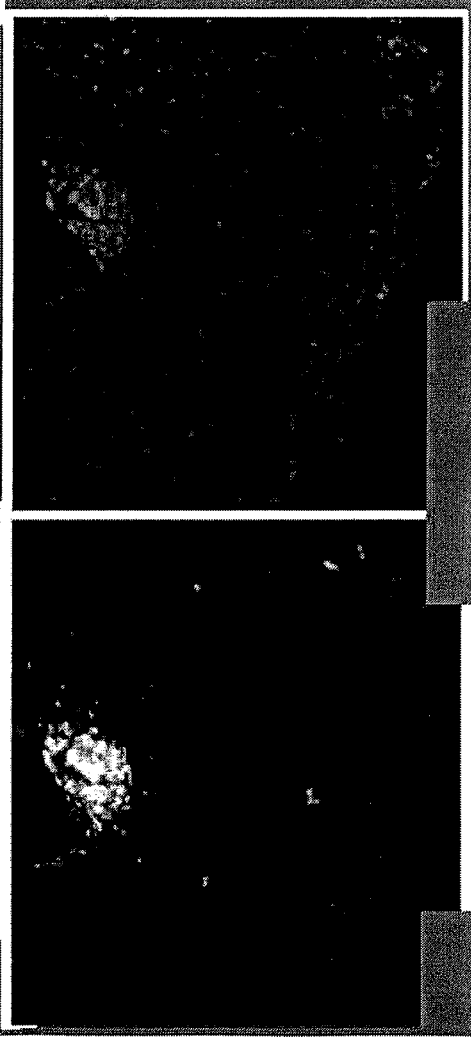
FIG. 3A₁ MLFC3F-nlacZ/B5-eGFP inoculus
FIG. 3A₂
FIG. 3A₃
FIG. 3A₄
FIG. 3A₅

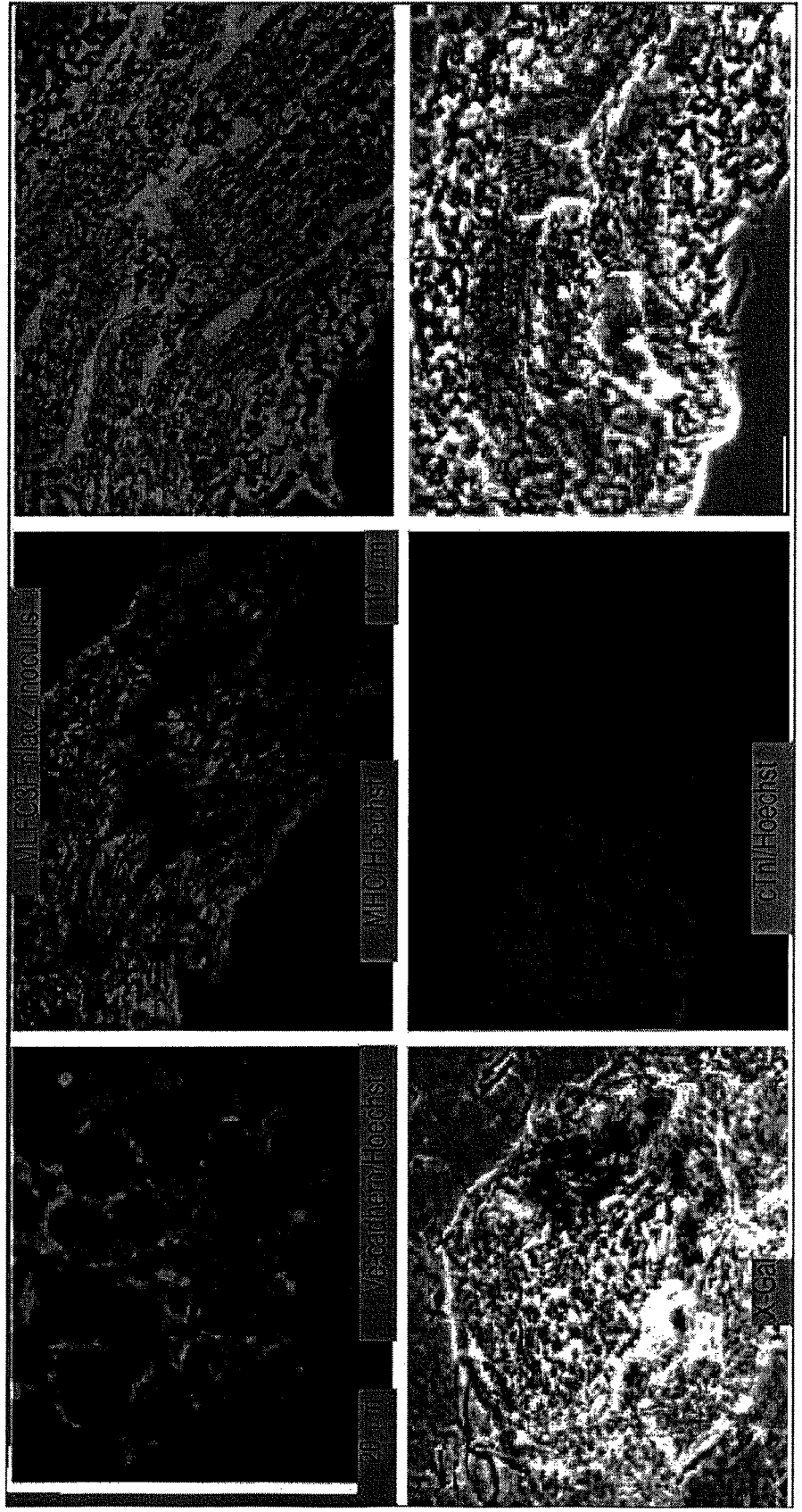

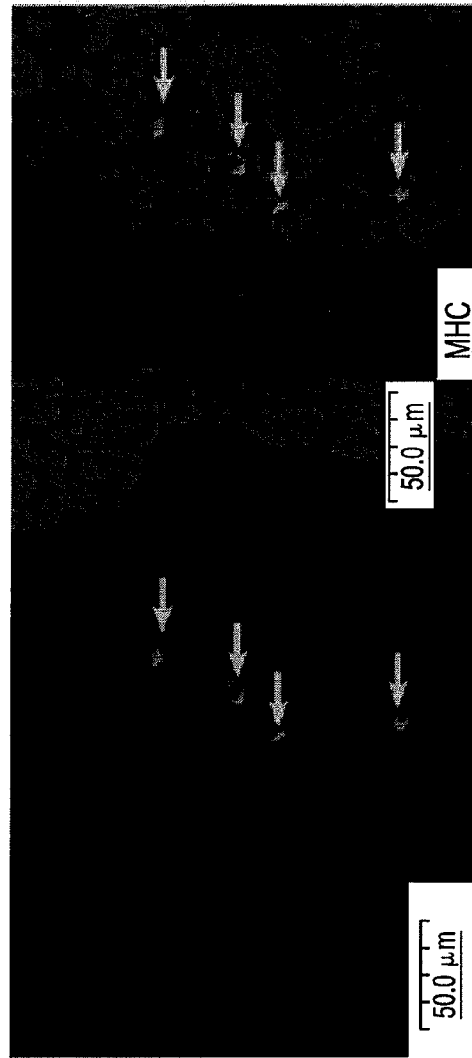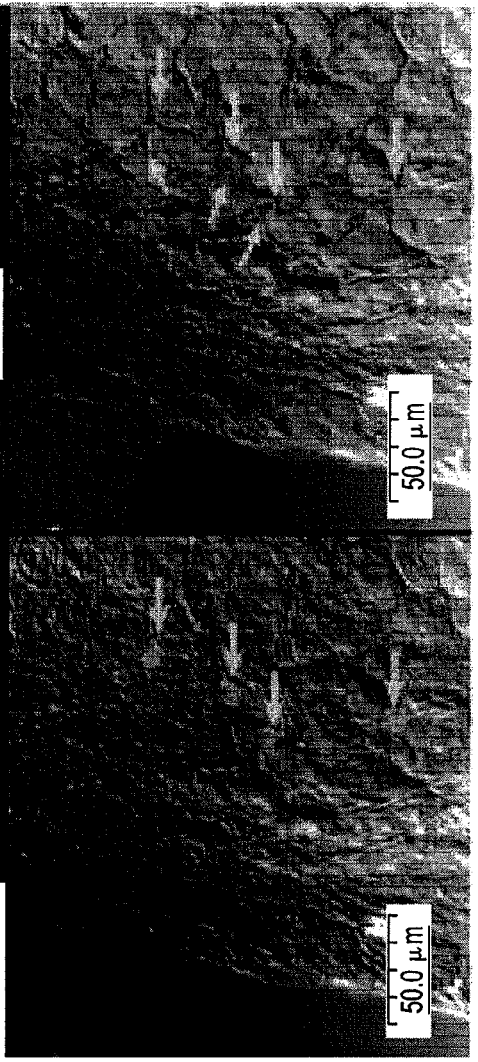
FIG. 3C₁  FIG. 3C₂  FIG. 3C₃  FIG. 3C₄

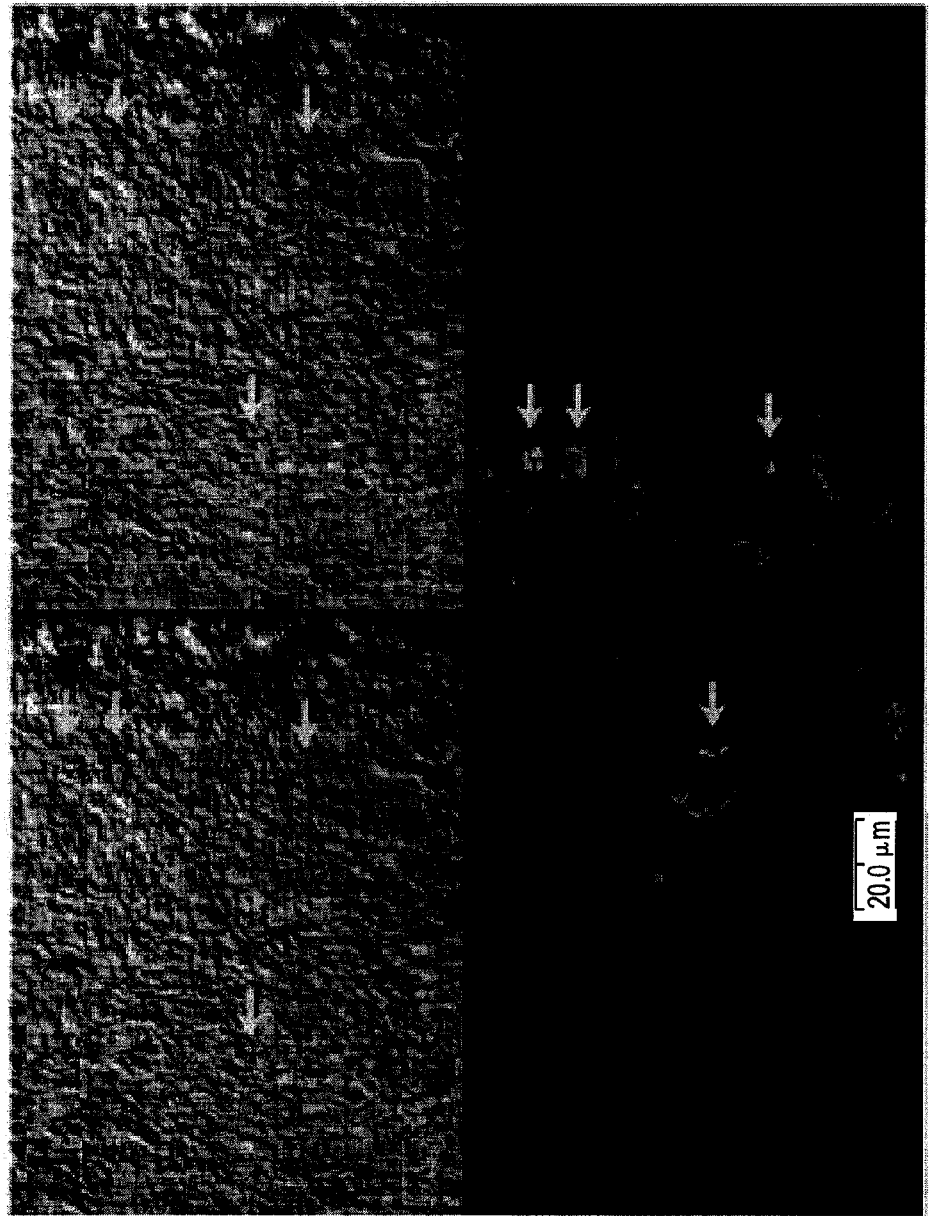

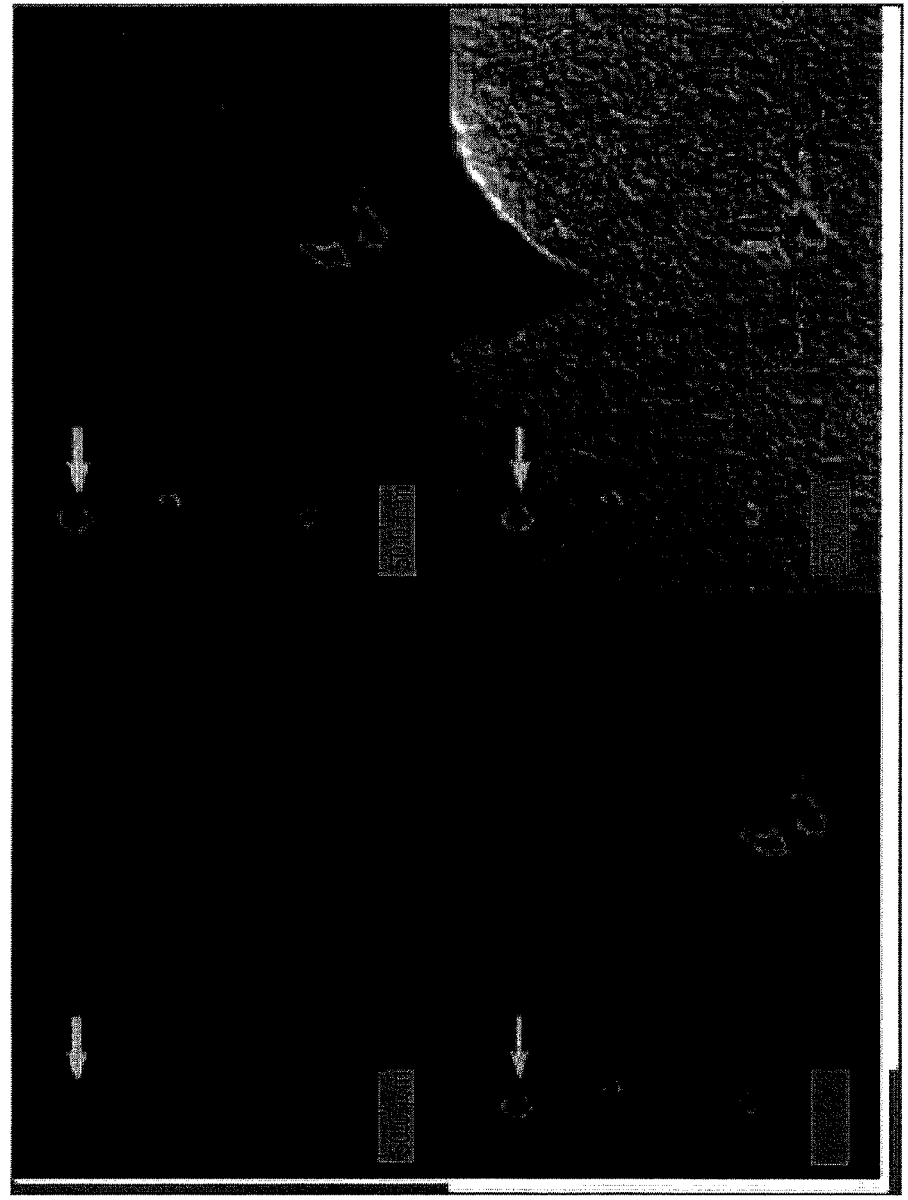

Table 1
Myocardial Repair (Echocardiography)

| | CAL+CSs (N=4) | CAL (N=6) | Sham (N=3) |
|---|---|---|---|
| LVIDd, mm | 4.10 | 3.57 | 2.13†  |
| | SD±0.85 | SD±0.33 | SD±0.06 |
| | SEM±0.42 | SEM±0.13 | SEM±0.03 |
| AWThd, mm | 0.80 | 0.60 | 1.03† |
| | SD±0.29 | SD±0.20 | SD±0.01 |
| | SEM±0.15 | SEM±0.08 | SEM±0.01 |
| FS, % | 36.85 | 17.87* | 59.13*† |
| | SD±16.43 | SD±5.95 | SD±4.56 |
| | SEM±8.21 | SEM±2.43 | SEM±2.63 |
| Regional wall motion abnormality, % | 33.82 | 30.88 | |
| | SD±10.05 | SD±14.71 | |
| | SEM±6.53 | SEM±7.35 | |

*P<0.05 vs CAL+CSs.
†P<0.05 vs CAL.
Effect of human CSs orthotopic transplantation on echocardiographic index of myocardial performance. Data are presented as mean±SD.
LVIDd indicates left ventricular internal dimension at end diastole; AWThd, anterior wall thickness; FS, fractional shortening.

FIG. 3D

CARDIAC STEM CELLS AND METHODS FOR ISOLATION OF SAME

CROSS-REFERENCE TO RELATED APPLICATIONS

This application is a continuation of U.S. application Ser. No. 10/567,008 filed Jul. 13, 2006 which is the U.S. National Phase application under 35 U.S.C. §371 of International Application PCT/IT2004/000421 filed Jul. 29, 2004, which claims priority to Italian Application RM2003 A 000376, filed Jul. 31, 2003. The entirety of each of these applications is hereby incorporated by reference.

BACKGROUND OF THE INVENTION

1. Field of the Invention

The invention concerns a method for the isolation and expansion of cardiac stem cells derived from postnatal cardiac tissue biopsy.

The invention deals with a method for the isolation, expansion and preservation of cardiac stem cells from human or animal tissue biopsy samples to be employed in cell transplantation and functional repair of the myocardium or other organs.

The cells may also be used in gene therapy, for treating genetic cardiomyopathies by expressing the healthy gene in cells from biopsies of subjects with genetic defects, propagating the cells in vitro and then transplanting them in the patient; for treating ischemic heart diseases by inducing the release of angiogenic growth factors by the transplanted cells; and for the setting of an in vitro models to study drugs.

2. Prior Art

Stem cells (SC) are able to replicate and to differentiate in response to appropriate signals, thus enabling the formation or regeneration of specialized tissues.

It was thought that cardiomyocytes were terminally differentiated cells; however, emerging evidence has shown the modest potential of these cells to proliferate in animal models and in heart transplant patients (1-4).

The limited ability of adult cardiomyocytes to undergo mitosis and to regenerate the myocardium after injury leads to a permanent deficiency in the number of functioning cells, with the development and progression of cardiac insufficiency. In the end stage of the disease, the alternative treatment to transplantation is the implantation of SC in the injured myocardium (cardiomyoplasty). This method has produced promising results in animal models and has been experimented also in humans. However, the problem of having a source and an availability of SC remains (5-7).

While embryonic SC (undifferentiated cells from the embryo that can produce a wide range of specialized cells and that can be derived from the cell mass inside blastocytes which, in humans, form 4-5 days after fertilization of the ovum) have a marked capability to proliferate and differentiate, their potential immunogenicity, arrhythmogenicity, and ethical issues in particular, have limited their use. Moreover, embryonic SC are pluripotent, consequently their use carries a potential risk of generating teratomas (as occurs in animal models). Hence, before these cells can be used, they need to be differentiated in vitro in cardiomyocytes.

There exist various types of cardiomyocytes (ventricular, atrial, sinus node, Purkinje, with pacemaker functions, etc.). Embryonic SC have the potential capability to generate these cardiomyocyte phenotypes in vitro but the yield is insufficient. Furthermore, the in vivo proliferative capability of cardiomyocytes derived from embryonic SC appears to be limited by the growth of multinucleate cells.

An alternative is to use adult SC (undifferentiated cells found in differentiated tissue that are able to proliferate, reproduce and differentiate into the specialized cell types of the tissues whence they were isolated) preferably obtained from the same patient, which would afford the advantage of allowing autologous transplantation without the need for immunosuppressive therapy. For this purpose, skeletal myoblasts (satellite cells) have been employed; however, they differentiate into skeletal myocytes with morphologic and functional properties differing from those of the cardiac muscle. The inability of skeletal myoblasts to transdifferentiate into cardiomyocytes and to couple with them could give rise to arrhythmias or other anomalies.

SC derived from bone marrow offer an attractive alternative, Mesenchymal SC (MSC) of the bone marrow can differentiate into cardiomyocytes in vitro (treated with DNA-demethylating agents) and in vivo where, however, in the presence of fibrosis, they mostly generate fibroblast-like cells. Hematopoietic SC (HSC) of the bone marrow (so-called side population cells [SPcells]) are pluripotent in that they can generate vascular epithelium, smooth muscle cells and cardiomyocytes. But the functional and electrophysiologic properties of HSC- and MSC-derived cardiomyocytes are not well characterized, and the use of undifferentiated cells instead of cardiomyocytes could give rise to in vivo differentiation into fibroblasts rather than muscle cells or to the development of tumors.

Although human cardiomyocytes have been conventionally considered terminally differentiated cells (i.e. unable to re-enter the cell cycle and to divide), indirect evidence accumulating over the past two years has suggested the existence of adult SC in the heart. These cells are ideal candidates for cardioplasty in that they need no reprogramming, give rise only to cells present in the heart, i.e. cardiomyocytes and vessels (endothelial cells and smooth muscles) and may, because this is their physiologic function, survive in transplant patients, integrate into the surrounding tissues and carry out their functions for longer periods without causing any damage. Patent applications WO 03/008535 and WO 03/006950 concern methods to derive cardiomyocytes from embryonic SC. Patent applications WO 02/13760 and WO 02/09650 deal with the use of adult SC (particularly hematopoietic and/or cardiac cells, without indicating a method to isolate them, also in combination) to repair cardiac injury or in treating cardiovascular diseases in general.

Patent application WO 99/49015 deals with the isolation of pluripotent cardiac SC of the adult p53−/− mouse. In particular, the description concerns the heart-derived pluripotent SC that differentiate and proliferate to produce a variety of cell types, including cardiocytes, fibroblasts, smooth muscle cells, skeletal muscle cells, keratinocytes, osteoblasts and chondrocytes. The cells may be employed in methods to treat patients with cardiac tissue necrosis. The SC proliferate and differentiate to produce cardiocytes that replace the necrotic tissue.

However, the method differs from that of the present invention, which was based on the assumption that the cardiac muscle cells, the striate muscles and the smooth muscle cells derived from a common precursor, the myoblast. Furthermore, there is no in vivo evidence from cardiomyopathic animals that supports the applicability of the method. Lastly, the methods differ substantially. In the method described in patent WO 99/49015, adult p53−/− mouse hearts are fragmented, dissociated with DNAse and collagenase. After centrifugation, the sediment myocytes are isolated on a discontinuous gradient (Percoll) and plated on a medium containing 5% FBS and then on a medium containing 15% FBS 20 days later. Between days 20 and 26, small (<5 μm) round, nonadherent, slow-growth, phase-bright cells with a high nucleus-to-cytoplasm ratio form in the suspension. These cells continue to live in the suspension for about 1.5 months in the presence of 10% horse serum. Then the cells remain suspended also without the addition of horse serum. The nonadherent SC do not form colonies in methylcellulose and proliferate in the presence of serum, SCF, aFGF, bFGF, and cFGF. In the absence of horse serum, the nonadherent cells differentiate into differently appearing adherent cells the authors have identified by mainly morphologic criteria as cardiocytes, chondrocytes, fibroblasts, smooth muscle cells, skeletal muscle myoblasts, pericytes, and other cells the authors have called adherent SC. About one fourth to one fifth of these cells is positive to alkaline phosphatase (osteoblasts and endothelial cells); all cells are negative to acetylated LDL (absence of endothelial cells) and to myosin heavy chain (MF20). The cells undergo mitosis when stimulated by bFGF, aFGF and cFGF. In the absence of serum, they differentiate into cells resembling a fried egg (myocytes), After treatment with ascorbic acid/α-GP, they differentiate into chondrocyte-like cells.

Adherent cells cloned by limiting dilution give rise to mesenchymal cells, including osteoblasts, chondrocytes, adipocytes and myocytes, although they cannot be clearly identified due to often inappropriate morphologic criteria and markers. All the cells tested negative to acetylated LDL (absence of endothelial cells). None of the 11 isolated clones could be induced to differentiate toward a single mesenchymal lineage.

The isolation of the cardiac-derived SC of neonate mice (1-4 days) is also described, wherein the passage of myocytes on human fibronectin is added to eliminate the fibroblasts. However, no data are given about the characteristics of the isolated SC. Furthermore, the cells isolated with the previous method do not give rise to the formation of an essential component of the heart tissues, i.e. vessels and endothelium.

DESCRIPTION OF THE INVENTION

The method of the present invention employs heart biopsy tissue as starting material, hence an elective material that cannot be used in the method described in patent application WO 99/49015, since the material was insufficient. After fragmenting the biopsy specimen and possibly using dissociating agents (e.g. trypsin, EDTA and collagenase), the fragments are plated and added to a medium containing 10% FBS; 10-30 days later, fibroblast-like adherent cells grow from the explants over which small round, phase-bright cells migrate that tend to cluster but are either not or only weakly adherent. The cells are isolated by washing and mild dissociation (e.g. EDTA, trypsin-EDTA for 2-3 min). The cells are then plated on polylysine-treated cellular substrates in an appropriate medium unlike that used in the previous technique, in that it is horse-serum-free and contains other growth factors; after 2-3 days cell aggregates (cardiospheres) arise that tend to grow as floating formations. The authors have found that the cardiac-forming cells are postnatal SC that can be advantageously employed for reimplantation in the myocardium.

These cells are able to multiply, while maintaining their origin characteristics for a period (at least 60 days) that is long enough to markedly enrich the cell population. Mechanical disaggregation of the cardiospheres (CS) by repeated pipetting and changing the medium every 3 days increases the number of CS (about 100-fold every 10 days) for at least the first 20 days. Given the number of SC that can be derived from a biopsy and their ability to multiply in vitro, it is thought that they can be used to replace a greater amount of tissue than that removed.

Certain cells in the CS present stem-cell markers (ckit, sca-1, CD34) that are able to differentiate toward the main components of the myocardium (cardiomyocytes and vessels). As evaluated by immunohistochemistry and/or RT-PCR, certain cells spontaneously express, particularly at the border of the CS, markers for cardiomyocyte (troponin I, ANP, myosin heavy chain) and for endothelial cells (von Willebrand factor and Ve-cadherin). The human CS, in a co-culture with rat myocytes, beat spontaneously. When inoculated subcutaneously in SCID mice, the murine CS give rise to growths containing cardiac muscle tissue and vessels within several days.

The authors have thus demonstrated that the SC can be derived in a reproducible manner from biopsy tissue of the atrium, ventricle and auricle of human subjects aged from 1 month to 70 years. The CS pertaining to the invention can be cryopreserved, and they maintain their functional characteristics after thawing.

Adult cardiac SC with similar characteristics can also be isolated from the mouse. In particular, to better understand cell differentiation in CS, several breeds of transgenic mice were studied; the findings confirmed the results obtained with human cells.

Lastly, the authors have shown in an animal model that human CS can be used for cardioplasty. When inoculated in the infarcted area (transthoracic cauterization or LAD ligation) of a SCID mouse, the cells give rise to cardiac tissue that presents good integration with the host tissue, as observed by morphology and immunohistochemistry studies.

Hence, the isolation and expansion of CS by the method of the invention is novel and advantageous compared with that described in the previous technique in terms of the origin of the sample, the methods of isolation and expansion and the morphologic and functional characteristics of the derived cells.

DETAILED DESCRIPTION OF THE INVENTION

The method comprises the following steps: biopsy sample obtained under sterile conditions and transported to the laboratory; preparation of fragments sized large enough to allow diffusion of nutrients present in the culture medium; distribution of fragments on culture plates and incubation under conditions appropriate for cell survival and growth; sampling of culture medium and cells and transfer to other culture plates under conditions adequate for cell expansion.

An object of the invention is a method to obtain stem cells able to repair damaged myocardiac tissue, comprising the following steps:

a) take a biopsy specimen of cardiac tissue and keep it in an appropriate culture medium;

b) treat the specimen under appropriate conditions with mild mechanical and/or chemical and/or enzymatic techniques to obtain tissue fragments sized large enough to allow the diffusion of nutrients present in the medium;

c) leave the tissue fragments to adhere to appropriate solid supports and maintain them in a medium containing convenient serum and/or growth factors;

d) allow the cells to grow, changing the medium partially or completely, until multicellular structures form that are either weakly adherent or do not adhere to the support;

e) separate said multicellular structures from the rest of the culture;

f) treat said multicellular structures by mild dissociation until most of the small phase-bright spherical cells detach but maintain their morphologic and functional characteristics;

g) plate the cells on culture substrates treated with polylysine or other agents promoting the adhesion of the culture to the support in a medium containing at least the minimal essential constituents for the growth of mammalian cells;

h) possibly repeat steps d) to g) at least once;

i) select the cells that aggregate in phase-bright spheroid formations (cardiospheres);

l) electively promote the formation of new cardiospheres by mild dissociation thereof and new formation;

m) eventually cryopreserve the cardiospheres for use after thawing.

Preferably stem cells are derived from non-embryonic cardiac tissue biopsies.

In one embodiment of the invention at least one of the steps follows treatment with oxygen concentrations different from that normally present in the atmosphere in order to modify the biologic characteristics of the cultures.

Experts in the field will understand that the CS derived with the procedure of the invention may be able to generate continuous cell lines following spontaneous transformation or transformation induced by chemical, physical or biologic agents.

In another embodiment the cells giving rise to and/or constituting cardiospheres are fused with other cells.

In another embodiment the cells giving rise to and/or constituting cardiospheres are used for nuclear transfer to and from other cells.

In another embodiment the cells giving rise to and/or constituting cardiospheres are grown in at least one stage on biodegradable and/or biocompatible supports.

In another embodiment the cells giving rise to and/or constituting cardiospheres are cultured in bioreactors and/or fermenters.

It is another object of the invention cells giving rise to and/or constituting cardiospheres able to repair myocardial tissue obtainable according to the method of previous claims. Preferably said cells are to be used in gene therapy. Preferably said cells are to be used for nuclear transfers to and from other cells. The CS derived with the method of the invention can be variously used in the repair of myocardial tissue, for nuclear transfer from and to other cells, in gene therapy for cardiopathies of genetic origin.

BRIEF DESCRIPTION OF FIGURES

FIG. 1—CS proliferation. $A_1$-$1A_4$) Phase micrographs of floating CSs (cultured from <24 h to >48 h) derived from a primary culture of a human atrial bioptical sample. $1B_1$-$1B_3$) Proliferation curves of human and mouse CSs (human CSs were derived from 8 different subjects ($1B_1$) and from pre- and post-natal mouse hearts ($1B_2$ and $1B_3$) respectively), in the presence ($1B_1$ and $1B_2$) and in absence ($1B_3$) of 3.5% serum. Number of spheres refers to the mean number per well from which 90% of the spheres where withdrawn at each time-point for further analysis. Note the different pattern of proliferation between the human and mouse CSs and the rapid rise of the curves, followed by an irreversible decline in the serum-free conditions. $1C_1$-$1C_4$) Fluorescence analysis of a single cell ($1C_2$) (obtained from a dissociated GFP-expressing CS), when plated by limiting dilution on mitomycin-treated STO-fibroblast-coated 96-wells plates in CGM, over the course of the generation of the GFP-labeled clone. This clone could be passaged and expanded on poly-D-Lysine coat ($1C_3$). $1D_1$-$1D_2$) x-Gal staining of a eGFP/MLC3F clone (obtained as those human) after 48 hours exposure of growth factors-free medium: in these conditions cells in the clone become more flattened with many nuclei showing a blue color, demonstrating that a differentiation process occurred.

FIG. 3—In vivo analysis. $3A_1$-$3A_5$) Ectopic transplantation in SCID mouse of CSs from MLC3F-nlacZ/BS-eGFP mouse ($3A_1$-$3A_5$). Fluorescence analysis of unfixed cryosections ($3A_1$-$3A_2$; $3A_4$) from the subcutaneous dorsal inoculum (day 17): GFP-cells seemed to have migrated from the spheres while clusters of vessel-like structures could be observed mainly in the external area (insert). Staining for SMA of one of these cryosections showed positive immunoreaction of the sphere and some cells within the inoculum ($3A_5$). $3B_1$-$3B_6$) Fluorescence ([;] $3B_1$, $3B_2$, and [$3B_4$] $3B_5$) and phase analysis ([;] $3B_4$ and [$3B_5$] $3B_6$) of fixed and immuno-stained cryosections from dorsal inoculum of CSs from MLC3F-nlacZ/CD-1 and cTnI-lacZ/CD-1 mice: tubular structures were stained for sarcomeric myosin and cTnI (middle and lower panels respectively). X-Gal staining labeled the cells within and those migrating from a CS ($3B_2$). Endothelial markers (SMA and Ve-cadherin), stained the vasculature ("black-holes") ($3B_1$; see also $3A_3$). $3C_1$-$3C_8$) Orthotopic transplantation on a SCID-bg mouse, of cryopreserved human CSs into the viable myocardium bordering a freshly produced infarct. Confocal analysis of cryosectioned left ventricular heart after 18 days from the coronary ligature, shows that ($3C_1$-$3C_4$) cardiomyocytes expressing MHC (red) in the regenerating myocardium (particularly those indicated by the two central arrows), stain positive also for lamin A/C (green) (a specific human nuclear marker). In these cells MHC expression is evident mainly in the perinuclear area. Lamin A/C-labeled cells (red) are present in newly generated capillaries staining for smooth a-actin (see $3C_9$-$3C_{12}$), and PECAM ($3C_5$-$3C_8$); connexin-43 (red) [0], as in the co-culture experiments, lines cytoplasmic membrane of some human cell (green) in the regenerating myocardium. 3D) Table 1. Effect of human CSs orthotopic transplantation on echocardiographic index of myocardial performance. Data are presented as mean±SD. Abbreviations: LVIDd, left ventricular internal dimension at end diastole; AWThd, anterior wall thickness; FS, fractional shortening; EF, ejection fraction. *: vs CAL+CSs $p<0.05$, §: vs CALp<0.05

METHODS AND MATERIALS

Tissue Samples

Figure 2H:
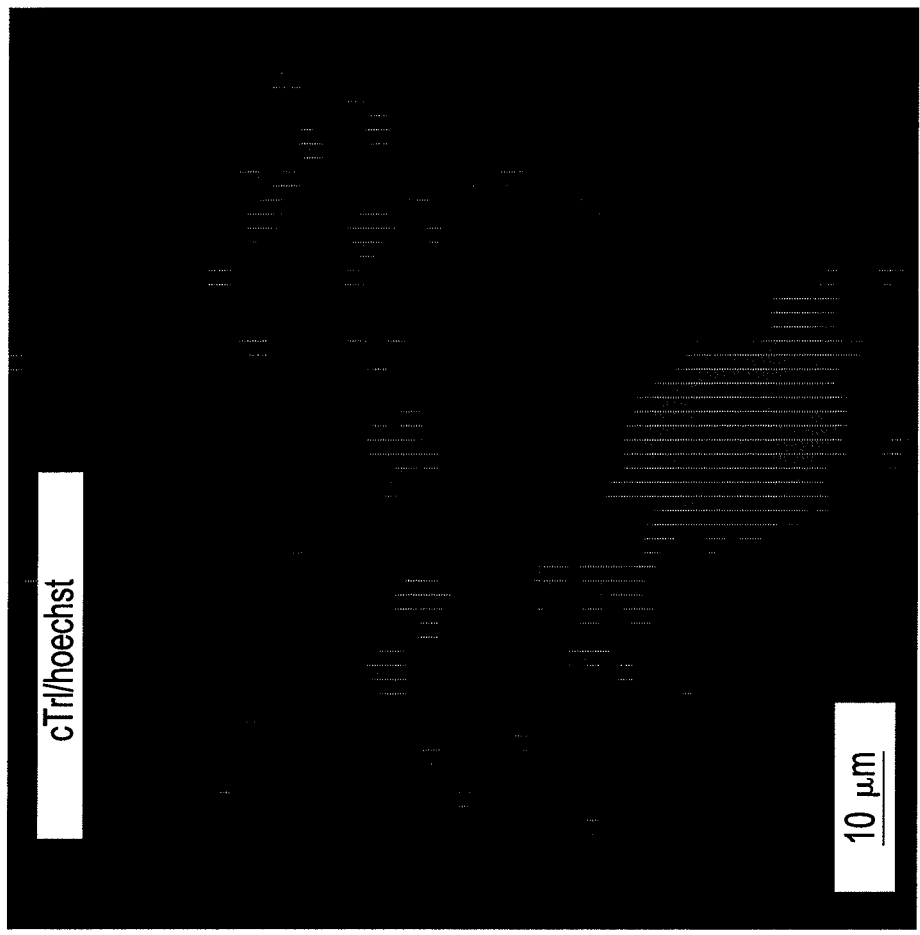
FIG. 2—CS characterization. $2A_1$-$2A_{10}$) Fluorescence-confocal analysis of BrdU-labeled human CSs for cardiac differentiation markers: 6 µm scans (from the periphery to the center of the sphere) and final pictures (small and large images respectively). BrdU (green; $2A_1$-$2A_{10}$), cTnI (red; $2A_1$-$2A_5$) and ANP (red; $2A_6$-$2A_{10}$). $2B_1$-$2B_4$) Confocal analysis of human CSs after 12 h of culture: CD-34 ($2B_4$), CD-31 ($2B_3$), KDR ($2B_2$) and c-Kit ($2B_1$) labeling of CS-generating cells at the beginning of sphere formation. $2C_1$-$2C_3$) Fluorescence phenotype analysis of human CSs (cryosections): cTnI (red; $2C_1$), sarcomeric myosin ($2C_2$) and vWf (green; $2C_3$). $2D_1$-$2D_2$), Fluorescence phenotype analysis of human partially dissociated-CSs, after four days of culture on collagen coat in CEM: cTnI (red; $2D_2$) expression appears in the cytoplasm of the human cells (migrated from the sphere) showing a triangular shape with a row arrangement). $2E_1$-$2E_3$) Fluorescence analysis of partially dissociated eGFP-labeled human CSs at 96 h of co-culture with rat cardiomyocytes: the same green cells that showed a synchronous contraction with cardiocytes, express cTnI. $2F_1$-$2F_3$) Fluorescent analysis of connexin-43 expression (red) in eGFP-labeled human CSs co-cultured with rat cardiomyocytes (as in panel e): a punctuate red fluorescence is present in the cell membrane of human cells. $2G_1$-$2G_6$) Phase micrograph of CSs from MLC3F-nlacZ ($2G_1$-$2G_2$) and cTnI-nlacZ mice ($2G_3$-$2G_6$): nuclear lacZ expression mainly localized in the external layers of both embryo ($2G_1$ and $2G_{3/4}$) and adult CSs ($2G_2$ and $2G_{5/6}$), after a short time from their formation ($2G_4$ and $2G_6$) and after a few days of culture. Nuclei of cells (derived from partially dissociated CSs, cultured for 5 days on collagen-coated surfaces) are also blue stained. 2H) Florescence analysis of a spontaneously differentiated mouse CS: as suggested from the synchronous contraction showed in culture, cTnI (red) is expressed in the sphere and the cells migrated; in the last, sarcomeres are also evident. $2I_1$-$2I_6$) Fluorescence and phase analysis of CSs from GFP-cKit ($2I_1$, $2I_2$, $2I_4$, and $2I_5$), GFP-cKit/MLC3F-nLacZ ($2I_3$) and GFP-cKit/cTnI-nlacZ ($2I_6$) mice. GFP-labeled cells were present a few minutes after their seeding in culture with CGM, at the beginning of the generation of the CSs, later in their inner mass and after their migration out from the oldest adherent spheres (arrows). GFP-labeled cells did not co-localize with the blue-stained ones (arrows) in CSs from GFP-cKit/MLC3F-nLacZ and GFP-cKit/cTnI-nlacZ mice; fluorescent cells were present also in the CSs' growth area (arrows) (right upper and lower panels; $2I_3$ and $2I_6$, respectively). Fluorescence, phase (small) and merged (large) images. $2J_1$-$2J_3$, FACS analysis of post-natal mouse CSs-derived cells. A time course at 0 and 6 days was performed and the phenotype profile for CD34, cKit, Cd31 and sca-1 expression was analyzed and showed as percentage of positive events ($2J_1$). Data are presented as mean±SD (n=3). *Indicates a statistically significant difference from T0.

The human tissue came from myocardiac biopsies of adult or other patients who underwent open heart surgery (aortocoronary bypass, cardiac valve replacement, tetralogy of Fallot, ventricular septum defect) or heart transplantation for advanced dilated cardiomyopathy or post-infarction chronic congestive cardiomyopathy. The murine tissue came from the hearts of previously characterized homozygous MLC3F-nLacZ mice (8) homozygous troponin-I-nLacZ (9) and EGFP/ckit (10) CD1-crossed mice. The mice show localized nuclear expression (cardiac and skeletal) of the trans gene for, β-galactosidase of the myosin light chain promoter, a tissue-specific nuclear expression (exclusively cardiac) of the trans gene for troponin-I and a cytoplasmic expression of the EGFP trans gene of the ckit promoter (the gene in these cell experiments), respectively. BS-EGFP mice (11), which show generalized expression of cytoplasmic GFP, were used as base strains. The crossed MLC3F-nLacZ/EGFP, MLC3F-nLac-Z/EGFP-ckit, Tn-I-nLac-Z/EGFP-ckit mice were bred according to experimental protocol. The human cardiac tissue biopsies were preserved in serum-free IMDM (Euroclone) at 00 C and maintained at this condition until arrival in the laboratory (within 2 h).

Processing, Isolation and Cryopreservation of Sphere-Forming Cell

After careful dissection of the macroscopically visible connective tissue, the samples were cut into 1-2 mm³ pieces, washed 3 times with $Ca^{++}/Mg^{++}$-free phosphate buffered solution (PBS, Invitrogen) and sequentially digested 3 times for S min each at 370 C with 0.2% trypsin (Gibco) and 0.1% collagenase IV (Sigma). The obtained cells, the bulk of which are elements of contaminating blood, were discarded and the remaining tissue fragments were washed with complete explant medium (CEM) [IMDM supplemented with 10% fetal calf serum (FCS) (Hyclone), 100 mg/ml penicillin, 100 U/ml streptomycin (Gibco), 2 mM L-glutamine (Gibco), 0.1 mM 2-mercaptoethanol (Sigma). The tissue pieces were then fixed to Petri dishes (Falcon) by light scraping with a scalpel on a plastic surface. The explants with cultured at 37° C. in 5% CO2 in complete IMDM. The murine cardiac tissues were treated similarly, except for the embryonic hearts, where enzyme digestion prior to explant digestion was omitted and the organs were partially dissociated with a 25 gauge needle. After a period of 1 to 3 weeks (depending on the origin of the sample, i.e. a shorter period for the embryonic tissue and a longer one for the adult tissue), a layer of fibroblast-like cells forms that derive from or surround the explants. The explants are then periodically treated (every 6-10 days, 4 times maximum) to isolate the sphere-forming cells. To remove only the phase-bright cells, which migrate from the explants to the outer cell layer, the medium is removed, and the material is collected by washing it twice with $Ca^{++}$—$Mg^{++}$-free PBS and once with 0.53 mM EDTA (Versene, Gibco) for 1-2 min, followed by mild trypsinization with 0.5 g/L-0, 53 mM Trypsin-EDTA (Gibco) at room temperature for another 2-3 min under visual microscopic control. After the cells are collected, complete medium is added to the explants, whereas the cells obtained by washing and enzymatic treatment are collected by centrifugation (1200 rpm for 7 min) and resuspended in cardiosphere-growing medium (CGM) (35% complete IMDM/65% DMEM-Ham's F-12 mix with 2% B27 [Gibco], 0.1 mM 2-mercaptoethanol, 10 ng/ml EGF (Prepotek EC, Ltd.), 40 ng/ml bFGF (prepotek EC, Ltd.), 4 nM cardiotrophin-1 (RD), 40 nM thrombin (Sigma) (final concentrations), antibiotics and L-Glu as in the complete medium. Depending on the number of cells obtained (from $10^4$ to $4\times10^5$ cells/explant), the cells were resuspended by repipetting them and then plating about $2\times10^5$ cells/ml on poly-D-lysine (BD) coated multi-well plates. After 12-24 h, several cells begin to divide and after 48 h, cell groups form that are often surrounded by a thin membrane and that can grow as floating spheres and adherent spheres. The growth medium is partially changed every 2-3 days, and the spheres are mechanically triturated using a pipette or 1 ml needles. For cryopreservation, the spheres (washed in $Ca^{++}$-$Mg^{++}$-free PBS and Versene) are resuspended in the freezing medium (complete IMDM/DMEM-Ham-F-12 50: 50, 5% B27, 10% DMSO). To calculate the growth curves, all the spheres are counted during the first week of growth, and then 90% of the spheres are removed at defined times (and used for RT-PCR or immunohistochemical analysis); after adding CGM and mechanically triturating the residual spheres, they are left to proliferate until the next sampling, when they are recounted. BrdU labeling is performed for 12 h on the newly generated spheres and at defined times in the other spheres, as indicated (Roche). For clonal analysis, the human CSs are infected with a third-generation lentiviral vector, pRRLsin.PPT-PGK.GFP expressing green fluorescent protein (GFP), as described elsewhere (12). After being washed twice, the GFP-labeled CSs are dissociated into single cells by trituration in $Ca^{++}$/

Mg$^{++}$-free PBS, Versene, and 1× trypsin-EDTA solutions in sequence, resuspended in CGM, and then seeded at a presumed concentration of 1 cell/well in 96-well plates coated with a feeder layer of mitomycin-C-treated STO fibroblasts (2 μg/ml), For differentiation on a substrate-coated surface, Ca$^{++}$/Mg$^{++}$-free PBS-washed, centrifuged and partially dissociated CSs are repeatedly pipetted and then seeded in a small volume of CEM (200-300 μl) on type I collagen-(Sigma) or Matrigel-(Falcon) coated dishes and cultured for 3-6 days.

In Vivo Analysis

For heterotopic transplantation, about 60 pooled CS obtained from pre- and postnatal EGFP/MLC3F-nLacZ or EGFP/TnI-nLacZ or MLC3F/nLacZ, TnI-nLacZ mice were washed twice in PBS and suspended in 100 μl of Matrigel (BD) and subcutaneously injected into the dorsal region of anesthetized (ketamine, 35 mg/kg i.m.) adult NOD-SCID mice. Transplanted-cardiosphere survival and function were monitored by direct palpation of beating through the skin. After about 3 weeks, the mice were sacrificed and the isolated inoculum was embedded in OCT for immunocytochemical analysis. After thawing, 10-day cultures of cryopreserved human CS derived from ventricular and atrial cardiac explants from adult subjects were used for orthotopic transplantation. About 20 washed and partially dissociated CS were suspended in 3 μl PBS and injected in the infarcted myocardiac area using a 27 gauge needle and a Hamilton syringe. Myocardiac infarction was induced as described elsewhere (13) with slight modifications. Briefly, the recipient NOD-SCID mice (anesthetized with ketamine [35 mg/kg]+xylazine [5 mg/kg] i.p.) underwent transthoracic cauterization (Surgitron 140 v) with a modified electrocautery probe inserted through the internal intercostal muscle in the fourth intercostal space on the anterior surface of the heart. Electrocauterization (ca. 40 W) was applied twice for 1 sec in the cutting mode before the CS were injected (the same volume of PBS was injected in the control mice). In some mice myocardial infarction has been also induced by LAD ligation. After about 3 weeks, the mice were sacrificed and the isolated heart was embedded in OCT after extensive washing in PBS and fixing with paraformaldehyde (4%) in PBS pH 7.4.

Immunocytochemistry

Immunocytochemistry on tissue sections and on cell cultures was performed as described elsewhere (14) using the following antibodies: monoclonal anti-human-cTnI, anti-human-cardiac-MHC, anti-human nucleus and polyclonal (PAb) anti-human ANP (Chemicon); mAb anti-CD-31, CD-34 (BD Biosciences), mAb anti-human Cripto-1 (RD), monoclonal anti-Ve-cadherin, anti-sea-I, mAb anti-mouse-cKit (Pharmigen), mAb anti-human-c-Kit (DAKO); pAb anti-human-von-Willebrand-factor and mAb anti-human-KDR (Sigma); mAb MF20 and pAb anti-mouse/human MHC (14), anti-desmine and anti-Smooth-Muscle-Actin (Sigma), mAb anti-humanimouse-cTnI (15), donated by S. Schiaffino (Dept. of Pathology, Univ. of Padua), pAb anti-mouse-flk-1 (Santa Cruz, USA). β-galactosidase activity was detected by light microscopy, as described elsewhere (14).

Reverse-PCR Transcription Analysis

Reverse-PCR transcription analysis was performed as described elsewhere (16). The oligonucleotides for amplifying the genes of the CS derived from the pediatric (PCS), adult subjects (aCS) and heart fragments (H) were the following:

```
hNkx2,5 (150 bp)
forw 5'-CTCCCAACATGACCCTGAGT-3'
and rev 5'-GAGCTCAGTCCCAGTTCCAA-3', hANF (350 bp)
forw 5'-AATCAAGTTCAGAGGATGGG-3'
and rev 5'-AATGCATGGGGTGGGAGAGG-3', hVe-Cad (330 bp)
forw 5'-TCTCTGTCCTCTGCACAA-3'
and rev 5'-ATGCAGAGGCTCATGATG-3', hGAPDH
forw 5'-GAAGAGCCAAGGACAGGTAC-3'
and rev 5'-CTGCACCACCAACTGCTTAG-3;
```

The oligonucleotides for amplifying the genes of the murine CS and the heart fragments (H) were the following:

```
mMHC (302 bp)
forw 5'-GAAGAGTGAGCGGCGCATCAAGGA-3'
and rev 5'-TCTGCTGGAGAGGTTATTCCTCG-3', m cardiac actin (494 bp)
forw 5'-TGTTACGTCGCCTTGGATTTTGAG-3'
and rev 5'-AAGAGAGAGACATATCAGAAGC-3', m cardiac TnC (410 bp)
forw 5'-AATGGATGACATCTACAAAG-3'
and rev 5'-TGAGCTCTTCAATGTCATCT-3'.

mGAPDH
forw 5'-CCTCTGGAAAGCTGTGGCGT-3'
and rev 5'-TTGGAGGCCATGTAGGCCAT-3'
```

Results

Isolation and Expansion of CS

Sphere-generating cells were obtained by mild enzymatic digestion of explanted human atrial or ventricular biopsies and fetal, embryo and postnatal mouse hearts. Soon after the generation of a layer of fibroblast-like cells from well adherent explants, small, round phase-bright cells began to migrate over this coat. These cells could be harvested periodically by treatment with EDTA and mild trypsinization, and allowed to grow on poly-D-lysine-coated culture surfaces, in a low-serum (3.5% FCS) medium supplemented with a serum substitute (B27), growth factors (EGF and bFGF), cardiothrophin-1 (CT-1) (17) and thrombin (18), which, in the first week of culture, led to a seven-fold increase in the number of spheres with respect to that obtained using the medium supplemented with the others factors either alone or in combination. Time course observations of cells derived from both human and murine explants showed that, early after their seeding (30 min), some of these cells began to divide while still in suspension; most cells became loosely adherent, others remained in suspension and some contaminating fibroblast-like cells attached firmly to the poly-D-lysine coat. Cellular divisions were evident also from the loosely adherent cell population and produced clusters of small, round phase-bright cells [that we termed cardiospheres (CSs)] after 10-12 hours (FIG. 1a). Within 24-36 hours from their appearance, CSs increased in size and some of them detached from the culture surface; after 48-72 hours most CSs were between 20 and 150 urn in size and, when not subjected to mechanical dissociation, the largest contained dark zones within their inner mass (FIG. 1a).

Murine CSs started a spontaneous rhythmic contractile activity soon after their generation and maintained this function during their life span, while human CSs did so only when co-cultured with rat cardiomyocytes. To be sure that contraction was a new trait acquired by the cs cells, gfp-labeled human CSs (partially or totally dissociated) were co-cultured with cardiomyocytes pre-stained or not with dil. Contracting gfp-labeled cells were observed after 48 hours of co-culture; furthermore, from this time onwards, a red color stained also the green fluorescent cells, suggesting that a connection is created between the human CSs and the rat cardiac cells. In fact, labeling of human cs/rat-cardiomyocyte co-cultures (in which only human cells were pre-labeled with gfp by lentiviral infection) with cx-43, the major ventricular gap junction protein, demonstrated the typical punctuate fluorescence pattern along the cytoplasmic membrane (FIG. 2f), indicating that a functional connection is created between the two cellular populations.

CSs were found to be composed of clonally derived cells and did not simply represent cellular aggregates. In fact, when human CSs [expressing the green fluorescent protein (GFP) after infection with lentiviral vectors expressing the reporter gene] or murine CSs (derived from eGFPIMLC3F or eGFP/cTnI-mice) were dissociated and plated as single cells on mitomycin-treated STO-fibroblast-coated 96-wells or at clonal dilution on 10 cm Ø Petri dishes, fluorescent spheres that could be sub-cloned on poly-D-lysine-coated surfaces (FIG. 1c) were generated with a 1 to 10% efficiency. These sub-clonally derived CSs show the same functional and phenotypic behavior in culture: after 3 days from their appearance, some murine clones started to, and after 48 hours of culture with CEM, the majority (6/7) of these showed expression of the lac-Z trans gene within nuclei after specific histochemical staining (FIG. 1d), Equally, human clones, derived from a single GFP-labeled cell, start a synchronous beating and express cTnI after 48 hours of co-culture with rat cardiomyocytes.

Furthermore, when BrdU was added to the culture medium, virtually all cells in the small, and those of the inner part of the largest CSs, were labeled (FIG. 2a), indicating that these cells were newly generated.

Human CS-generating cells were capable of self-renewal. With periodical dissociation, together with partial substitution of the growth medium every 2-3 days, a log-phase expansion of spheres was obtained (FIG. 1b). Growth was slower for mouse CSs (owing, probably, to the more differentiated features assumed in culture such as beating) and, serum-dependent (FIG. 1b) as for the human ones.

As shown in FIG. 2a, confocal immunofluorescence analysis of BrdU labeled human CSS with anti-BrdU (green) and cardiac-troponin i (ctni) or atrial natriuretic peptide (anp) (red), revealed BrdU-positive cells particularly in the inner part of the spheres, while ctni- or anp-positive cells were mainly localized in the external layers. Furthermore, several cs-cells expressed cardiac differentiation markers (ctni, anp) while still dividing, as indicated by BrdU incorporation (FIG. 2a), suggesting that early cardiac differentiation already occurred during the log-phase growth; generally, within 2-3 weeks, some spheres became adherent, showing a more flattened morphology. Some small cells eventually migrated out from these "sun-like" spheres in the form of adherent (differentiated) or small, round cells that could generate new spheres. After thawing from cryopreservation, CSs proliferated again, maintaining their propensity to beat.

Phenotypic analysis of newly developing human and mouse CSs revealed expression of endothelial (KDR (human)/flk-1 (mouse), CD-31) and stem-cell (CD-34, ckit, sca-1) markers. As shown in FIG. 2b, CSs at the 2-10 cell stage, strongly reacted with antibodies against these antigens. In larger spheres, the expression pattern of some of these markers (particularly cKit) was similar to the BrdU labeling (positive staining in the center and in some peripheral zones generating satellite spheres).

A time course (0 and 6 days) of the quantitative characterization of CSs cells with these stem and endothelial markers was performed by FACS analysis (FIG. 2l: as shown, at the beginning of their formation (T 0) the phenotype of these cells seems to reflect the epi-fluorescent microscopy analysis with about 10% of positive staining for all four phenotypes. However, at 6 days (T6) cKit appears as the only conserved marker, suggesting that the cKit$^+$ cells could be the main ones contributing to the maintenance of proliferation, while the initial positivity to the others may reflect an early activation state, as has been indicated for CD-34 in several system (19). Fluorescence microscopy analysis, performed on cryo-sectioned human CSs revealed expression of cardiac-differentiation markers (cTnI, MHC) and also of endothelial markers [von Willebrand factor (vWf)] (FIG. 2c). When totally or partially dissociated into single-cells and cultured on collagen-coated dishes, in the same medium as the explants, mouse and humans CS-derived cells assumed a typical cardiomyocyte morphology, phenotype (FIG. d-d$_1$, h) and function documented (in the mouse only) by spontaneous contraction.

As aforementioned, human CSs did not beat spontaneously; however, these began to beat within 24 h when co-cultured with postnatal rat cardiomyocytes, losing, after this time, their spherical shape and assuming a "sun-like" appearance. Markers of cardiac differentiation were co-expressed within GFP in human labeled CSs-cells (FIG. 2e).

To follow the differentiation process of CSs during-the pre- and post-natal age, MLC3F-nlacZ and cTnI-nlacZ mice were utilized (8,9). These mice express a form of lacZ transgene that localizes within the nucleus under the skeletal and cardiac muscle myosin light chain or cardiac troponin I promoter, respectively. CSs obtained from embryonic day 9-12, fetal day 17-18, neonatal and adult mice, showed spontaneous expression of the reporter gene in a variable percentage (10-60%) of spheres in the different culture conditions employed (FIG. 2e); moreover, as for the human ones, CS-generating cells from mice expressed stern (CD-34, sea-L, cKit) and endothelial cell markers (flk-1 CD-31).

On this basis, we utilized transgenic mice expressing the green fluorescent protein (GFP) under the control of the c-kit promoter (10), in order to further clarify the cellular origin of these spheres and to follow the pattern of their growth process. As shown in FIG. 2i, GFP-positive cells were present from the beginning of the formation of the CSs and, albeit with reduced fluorescence intensity, also later, within the mass of cells of the CSs and in cells migrating from old "sun-like" adherent CSs. Moreover, as suggested by the growth pattern of human CSs, when satellite secondary CSs appeared to detach from the primary ones, GFP-positive cells localized on the margins of the latter and in the inner part of the former.

We studied this process in double-heterozygous mice obtained from GFP-cKitIMLC3F-nlacZ or GFP-cKit/cTnI-nLacZ crossings: as shown in FIG. 2i, beta-Gal-positivity did not co-localize with GFP in cells present within the growing areas.

In conclusion, CSs appear to be a mixture of cardiac stem cells, differentiating progenitors and even spontaneously differentiated cardiomyocytes. Vascular cells were also present, depending on the sphere's size and time in culture. It is possible that, as for neurospheres (20), differentiating/differentiated cells stop dividing and/or die while stem cells continue to proliferate in an apparent asymmetric way, giving rise to many secondary spheres and to exponential growth in vitro. Mechanical dissociation favors this process. Death, differentiation and responsiveness to growth factors of the different cells within the CS, could depend on its three-dimensional architecture and on localization within the CS (21-22). The spontaneous formation of spheres is a known prerogative of neural stem cells, some tumor cell lines (LM) (22), endothelial cells (23) and fetal chicken cardiomyocytes (24). All these models (ours included), that mimic the true three-dimensional architecture of tissues, consist of spheroids of aggregated cells which develop a two-compartment system composed of a surface layer of differentiated cells and a core of unorganized cells that first proliferate and thereafter disappear over time (perhaps through apoptotic cell death). As well documented in fetal chick cardiomyocytes and endothelial cell spheroid culture, three-dimensional structure affects the sensitivity of cells to survival and growth factors (22,23). In particular, central spheroid cells do not differentiate and are dependent on survival factors to prevent apoptosis, while the cells of the surface layer seem to differentiate beyond the degree that can be obtained in two dimensional culture and become independent of the activity of survival factors. Furthermore, cell-cell contact and membrane-associated factors are known to be important for the division of neural precursor cells (25), in accordance with the notion that stem cells will only retain their pluripotency within an appropriate environment, as suggested by the "niche" hypothesis (26).

To investigate the survival and morpho-functional potential of the CSs in vivo, two sets of experiments were performed: in the first, CS cells were injected in the dorsal subcutaneous region of SCID mice; in the second, they were injected into the hearts of SCID-beige mice, acutely after myocardial infarction. The intention of ectopic transplantation experiments was to study the pattern and the behavior of growth of CSs in a neutral milieu (i.e. one without specific cardiac induction), in order to verify their unique potential of generation of the main cardiac cell types and to exclude the possibility of neoplastic transformation. For these experiments about 60 pooled spheres/inoculum/mouse from pre- and post-natal MLC3F-nlacZ/B5-eGFP TnI-nlacZ/B5-eGFP mice or MLC3F-nlacZ/CD-1 and cTnI-nlacZ/CD-1 mice, were employed. During the first 10 days, beating was appreciable through the skin over the injection site, distant from large blood vessels. On day 17, animals were sacrificed and the inoculum recognized as a translucent formation, grain-like in size, wrapped in ramified vessel-like structures. Observation of unfixed cryosections by fluorescence microscopy revealed the presence of open spheres from which cells appeared to have migrated; clusters of "black holes", particularly in the periphery of the structure, were evident. The tissue contained tubular formations, surrounded by nuclei (Hoechst-positive), identified as cardiac sarcomeres because they were positive for cTnI and sarcomeric myosin (FIG. 3a). Alpha-SMA-positive structures (known to be transiently expressed during cardiomyogenesis (27)), were present in the remainder of the spheres and associated with the vasculature (the clusters of "black-holes"): this exhibited well-differentiated structures with a thin endothelium expressing Ve-cadherin (FIG. 3a) and a relative large lumen containing erythrocytes, indicating the establishment of successful perfusion by the host. Light microscopic observation of the inoculum, after X-Gal staining, showed strong nuclear expression of striated muscle-specific lacZ in the remainder of the spheres and in some cells close to them. No multi-differentiated structures suggesting the presence of tumor formation were observed.

To test the acquisition of functional competence and the cardiac regenerative potential of the CSs when challenged into an infarcted myocardium, orthotopic transplantation experiments with human CSs were performed. To do this, thawed (cryo-preserved) adult human CSs, coming from three atrial (one male and two female) and one ventricular (one female) biopsies were injected into the viable myocardium bordering a freshly produced infarct. Each mouse received CSs from a single passage of an explant (derived from a single subject). Four control infarcted animals were injected with an equal volume of PBS. After eighteen days from the intervention, the animals were sacrificed and infarct size was determined. Infarct size was 34.9±7.1 (3.6) and 31.9±6.9 (3.5) in the CS-treated group and PBS-injected group, respectively (p=n.s.). However, echocardiography showed better preservation of the infarcted anterior wall thickness (0.80±0.29(0.15) versus 0.60±0.20(0.08) p=n.s.) and particularly of FS % (36.85±16.43 (8.21) versus 17.87±5.95 (2.43) p<0.05) in the CS-treated group compared to the PBS-injected group (FIG. 3-table 1).

At the time of evaluation, bands of regenerating myocardium were present (with different degrees of organization and thickness) throughout most of the infarcted areas, as evaluated with hematoxylin-eosin histochemistry and MHC immunofluorescence (FIG. 3c). In the regenerating myocardium, cells expressing lamin A/C (a specific human nuclear marker) co-localize also with cardiomyocytes stained positive for MHC, newly generated capillaries stained for smooth a-actin and PECAM (FIG. 3c), and with connexin-43 expressing cells (which, as in the co-culture experiments, defines a connection between the human cells and the regenerating myocardium).

Thus CSs can be considered as clones of adult stem cells, maintaining their functional properties in vitro and in vivo also after cryo-preservation.

While this manuscript was in preparation, two papers have been published concerning the isolation of cardiac stem or progenitor cells from adult mammalian heart (28, 29). Isolation of these cells was based exclusively on the expression of a stem cell-related surface antigen: c-kit in the first paper and Sca-1 in the second one. In the first study (28) freshly isolated c-kit$^{pos}$ Lin$^-$ cells from rat heart were found to be self-renewing, clonogenic and multipotent, exhibiting biochemical differentiation into the myogenic, smooth muscle cell, or endothelial cell lineage but, differently from cells grown under the conditions described here, failed to contract spontaneously. When injected into an ischemic heart these cells regenerated functional myocardium. In the second study (29), Sca-1$^+$ cKit$^{neg}$ cells from mice heart were induced in vitro to differentiate toward the cardiac myogenic lineage in response to 5'-azacytidine. When given intravenously after ischemia/reperfusion, these cells homed to injured myocardium and differentiated into cardiomyocytes with and without fusion to host cells. Our data obtained on GFP-cKit transgenic mice also suggest that the adult cardiac stem cell is cKit$^{pos}$. It is possible that CSs enclose a mixed population of cells that, as a niche, could promote the viability of cKit progenitors and contribute to their proliferation. The data obtained in the present paper confirm the existence of an adult cardiac stem cell. More importantly, they demonstrate for the first time that it is possible to isolate cells from very small fragments of human myocardium and expand these cells in vitro many fold (reaching numbers that would be appropriate for in vivo transplantation in patients) without loosing their differentiation potential, thus opening previously unforeseen opportunities for myocardial repair.

Transgenic Mice

Figures 4A, 4B:
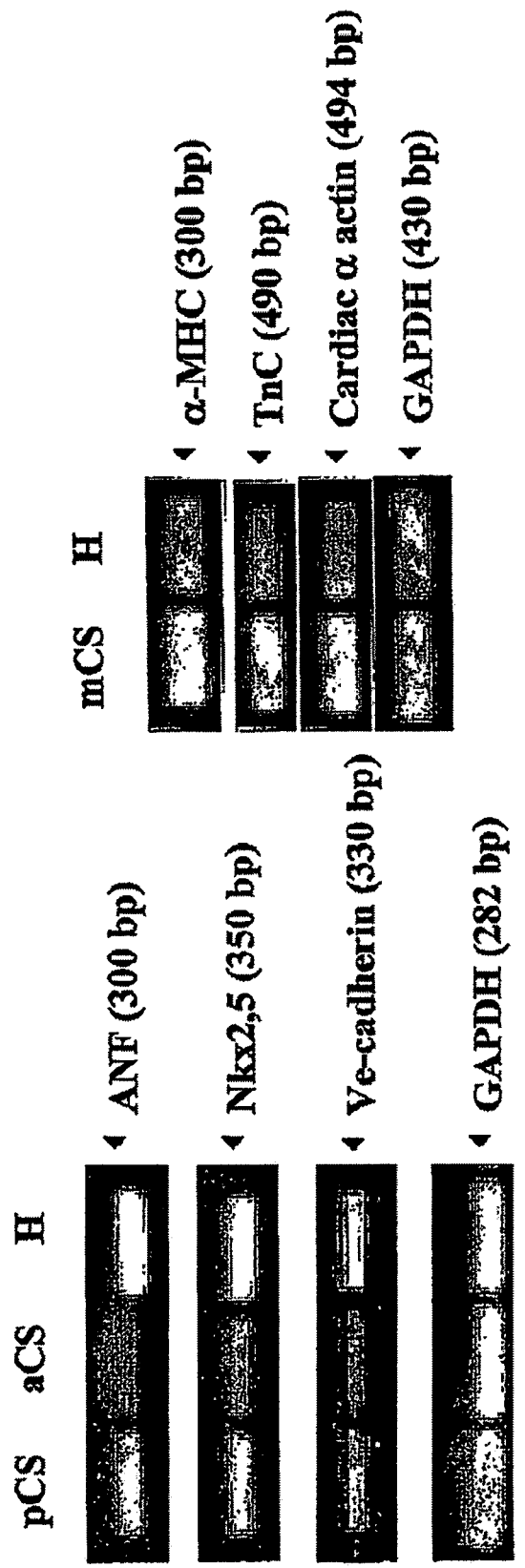
FIGS. 4A-4B. 4*a*) (left) RT-PCR analysis of human CS from pediatric (PCS), adult (aCS) subjects and cardiac fragments (H) (ANF, NKx2.S, Ve-cadherin, GAPDH), and 4*b*) (right) RT-PCR analysis of murine CS (mCS) and of mouse heart fragments (H) (α-MHC, TnC, cardiac a-actin, GAPDH).

To follow the differentiation process of CSs during the pre- and post-natal age, MLC3F-nlacZ and TnI-nLacZ mice were utilized. These mice express a form of the lacZ transgene that localizes within the nucleus under the skeletal and cardiac muscle myosin light chain or cardiac troponin-I promoter, respectively (8, 9). CSs derived from embryonic day 9-12, fetal day 17-18, neonatal and adult mice, showed spontaneous expression of the reporter gene in a variable percentage (10-60%) of spheres at the different culture conditions employed (FIG. 4a). Moreover, the mouse CS start to beat at the start of formation (particularly in the embryo) and continue to beat over the course of their life span. The human CS expressed stem (CD-34, sea-L, cKit) and endothelial cell markers (flk-1, CD-31).

In order to further clarify the cellular origin of these spheres and to follow the pattern of their growth process, we utilized transgenic mice expressing the green fluorescent protein (GFP) under the control of the c-kit promoter (10). GFP-positive cells were present from the beginning of the formation of the CSs and, albeit with reduced fluorescence intensity, also later. Moreover, as suggested by the growth pattern of human CSs, when satellite secondary CSs appeared to detach from the primary ones, GFP-positive cells localized on the margins of the latter and in the inner part of the former. We studied this process in double-heterozygous mice obtained from EGFP-cKit/MLC3F-nlacZ or TnI-nLacZ crossings. As shown in FIG. 4b, beta-Gal-positivity did not co-localize with EGFP in cells present within the growing areas.

Genetic Phenotype

The RT-PCR panel created on murine or human CS RNA extracts is shown in FIG. 5. A more typical profile of cardiac progenitors seems to be that of the human samples (in log-growth phase) compared with the murine samples, in which it is easier to have proliferation and differentiation occurring together.

REFERENCES

1. Soonpaa M H, Field L J. Survey of studies examining mammalian cardiomyocyte DNA synthesis. Circ Res. 1998 Jul. 13; 83(1):15-26.
2. Nadal-Ginard B, Kajstura J, Leri A, Anversa P. Myocyte death, growth, and regeneration in cardiac hypertrophy and failure. Circ Res. 2003 Feb. 7; 92(2):139-50.
3. Laflamme M A, Myerson D, Saffitz J E, Murry C E. Evidence for cardiomyocyte repopulation by extracardiac progenitors in transplanted human hearts. Circ Res. 2002 Apr. 5; 90(6):634-40.
4. Glaser R, Lu M M, Narula N, Epstein J A. Smooth muscle cells, but not myocytes, of host origin in transplanted human hearts. Circulation. 2002 Jul. 2; 106(1):17-9.
5. Reffelmann T, Kloner R A. Cellular cardiomyoplasty-cardiomyocytes, skeletal myoblasts, or stem cells for regenerating myocardium and treatment of heart failure? Cardiovasc Res. 2003 May 1; 58(2):358-68.
6. Dowell J D, Rubart M, Pasumarthi K B, Soonpaa M H, Field L J. Myocyte and myogenic stem cell transplantation in the heart. Cardiovasc Res. 2003 May 1; 58(2):336-50.
7. Passier R, Mummery C. Origin and use of embryonic and adult stem cells in differentiation and tissue repair. Cardiovasc Res. 2003 May 1; 58(2):324-35.
8. Kelly R, Alonso S, Tajbakhsh S, Cossu G, Buckingham M. Myosin light chain 3F regulatory sequences confer regionalized cardiac and skeletal muscle expression in transgenic mice. J Cell Biol. 1995 April; 129(2):383-96.
9. Di Lisi R, Millino C, Calabria E, Altruda F, Schiaffino S, Ausoni S. Combinatorial cis-acting elements control tissue-specific activation of the cardiac troponin I gene in vitro and in vivo. J Biol Chem. 1998 Sep. 25; 273(39):25371-80.
10. Cairns L A, Moroni E, Levantini E, Giorgetti A, Klinger F G, Ronzoni S, Tatangelo L, Tiveron C, De Fe lici M, Dolci S, Magli M C, Giglioni B, Ottolenghi S. c-kit regulatory elements required for expression in developing hematopoietic and germ cell lineages. Blood. 2003 Dec. 1; 102(12):3954-62.
11. Hadjantonakis A K, Gertsenstein M, Ikawa M, Okabe M, Nagy A. Generating green fluorescent mice by germline transmission of green fluorescent ES cells. Mech Dev. 1998 August; 76(1-2):79-90.
12. Follenzi A, Ailles L E, Bakovic S, Geuna M, Naldini L. Gene transfer by lentiviral vectors is limited by nuclear translocation and rescued by HIV-1 pol sequences. Nat Genet. 2000 June; 25(2):217-22.
13. Brooks W W, Garibaldi B A, Conrad C H. Myocardial injury in the mouse induced by transthoracic cauterization. Lab Anim Sci. 1998 August; 48(4):374-8.
14. Tajbakhsh S, Vivarelli E, Cusella-De Angelis G, Rocancourt D, Buckingham M, Cossu G. A population of myogenic cells derived from the mouse neural tube. Neuron. 1994 October; 13(4):813-21.
15. Ausoni S, Campione M, Picard A, Moretti P, Vitadello M, De Nardi C, Schiaffino S. Structure and regulation of the mouse cardiac troponin I gene. J Biol Chem. 1994 Jan 7; 269(1):339-46.
16. Ferrari S, Molinari S, Melchionna R, Cusella-De Angelis M G, Battini R, De Angelis L, Kelly R, Cossu G. Absence of MEF2 binding to the AfT-rich element in the muscle creatine kinase (MCK) enhancer correlates with lack of early expression of the MCK gene in embryonic mammalian muscle. Cell Growth Differ. 1997 January; 8(1):23-34.
17. Pennica D, King K L, Shaw K J, et al. Expression cloning of cardiotrophin1, a cytokine that induces cardiac myocyte hypertrophy. Proc Natl Acad. Sci USA. 1995; 92: 1142-1146.
18. Sabri A, Guo J, Elouardighi H, Darrow A L, Andrade-Gordon P, Steinberg S F. Mechanisms of protease-activated receptor-4 actions in cardiomyocytes. Role of Src tyrosine kinase. J Biol Chem. 2003 Mar. 28; 278(13):11714-20.
19. Zammit P S, Beauchamp J R. The skeletal muscle satellite cell.: stem cell or son of stem cell? Differentiation 2001; 68: 193-204.
20. Galli R, Gritti A, Bonfanti L, Vescovi M. Neural Stem Cells: An Overview. Circ Res. 2003; 92: 598-608.
21. Layer P G, Robitzki A, Rothermel A, Willbold E. Of Layers And Spheres: The Reaggregate Approach In Tissue Engineering. Trends Neurosci. 2002; 25:131-134.
22. Bates R C, Edwards N S, Yates J D. Spheroids And Cell Survival. Crit Rev Oncol Hematol. 2000; 36:61-74.

23. Korff T, Augustin H G. Integration Of Endothelial Cells In Multicellular Spheroids Prevents Apoptosis And Induces differentiation. J cell biol. 1998; 143:1341-1352.
24. Armstrong M T, Lee D Y, Armstrong P B. Regulation Of Proliferation Of The Fetal Myocardium. Dev Dyn. 2000; 219:226-36.
25. Svendsen C N, Ter Borg M G, Armstrong R J, Rosser A E, Chandran S, Ostenfeld T, Caldwell M A. A New Method For The Rapid And Long Term Growth Of Human Neural Precursor Cells. J Neurosci Methods. 1998; 85:141-152.
26. Schofield R. The Relationship Between The Spleen Colony-Forming Cell And The Haemopoietic Stem Cell- .Blood Cells. 1978; 4:7-25.
27. Kruithof B P, Van Den Hoff M J, Tesink-Taekema S, Moorman A F Recruitment Of Intra- And Extracardiac Cells Into The Myocardial Lineage During Mouse Development. Anat Rec. 2003; 271a: 303-314.
28. Beltrami A P, Barlucchi L, Torella D, Baker M, Limana F, Chimenti S, Kasahara H, Rota M, Musso E, Urbanek K, Leri A, Kajstura J, Nadal-Ginard B, Anversa P. Adult Cardiac Stem Cells Are Multipotent And Support Myocardial Regeneration. Cell. 2003; 114:763-776.
29. Oh H, Bradfute S B, Gallardo Td, Nakamura T, Gaussin V, Mishina Y, Pocius J, Michael Lh, Behringer Rr, Garry Dj, Entman M I, Schneider Md. Cardiac Progenitor Cells From Adult Myocardium: Homing, Differentiation, And Fusion After Infarction. Proc Natl Acad Sci USA. 2003; 100: 12313-12318.

What is claimed is:

1. A method for obtaining cardiospheres from a cardiac tissue biopsy sample, said method comprising the following steps:
    fragmenting a cardiac tissue biopsy sample to generate a plurality of cardiac tissue fragments; wherein the cardiac tissue biopsy sample is a non-embryonic cardiac tissue obtained from the ventricle, atrium or auricle of a heart;
    removing non-cardiac tissue or non-cardiac cells from said cardiac tissue fragments by partial enzymatic digestion of said cardiac tissue fragments;
    discarding said non-cardiac tissue or non-cardiac cells and retaining said partially digested cardiac tissue fragments;
    culturing said partially digested cardiac tissue fragments until phase-bright cells migrate from said cardiac tissue fragments;
    collecting said phase-bright cells;
    culturing said phase-bright cells on a treated surface in a culture media comprising 3.5% serum to generate one or more cardiospheres;
    wherein the one or more cardiospheres are spheroid structure of about 20 µm to about 150 µm in culture,
    wherein said cardiospheres are multicellular aggregates comprising stem cells, cardiac cells, and endothelial cells,
    wherein said stem cells express one or more stem cell markers selected from the group consisting of CD-34, ckit, and sca-1 within 12 hours of said cardiospheres being generated,
    wherein said endothelial cells express one or more endothelial markers selected from the group consisting of KDR, flk-1 and CD31 within 12 hours of said cardiospheres being generated; and
    harvesting said one or more cardiospheres, thereby obtaining cardiospheres.

2. The method of claim 1, wherein said removing further comprises dissection of said cardiac tissue biopsy sample.

3. The method of claim 1, wherein said partial enzymatic digestion is performed using trypsin, collagenase, or combinations thereof.

4. The method of claim 1, wherein said culture media comprises one or more of epidermal growth factor (EGF), fibroblast growth factor (FGF), cardiotropin-1, and thrombin.

5. The method of claim 1, further comprising disaggregating said harvested cardiospheres to generate disaggregated cells and culturing said disaggregated cells in said culture media to generate additional cardiospheres.

6. The method of claim 5, wherein said disaggregated cells are cultured on said treated growth surface.

7. The method of claim 1, wherein said treated growth surface comprises polylysine.

8. The method of claim 1, wherein said culture media comprises a serum substitute.

9. The method of claim 8, wherein said serum substitute comprises B27.

10. The method of claim 1, wherein said culture media is horse serum free.

11. The method of claim 10, wherein said culture media further comprises growth factors.

\* \* \* \* \*

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: hNkx Forward Primer

<400> SEQUENCE: 1
ctcccaacat gaccctgagt                                              20

<210> SEQ ID NO 2
<211> LENGTH: 20
<212> TYPE: DNA
<213> ORGANISM: Artificial Sequence
<220> FEATURE:
<223> OTHER INFORMATION: hNkx Reverse Primer

<400> SEQUENCE: 2
gagctcagtc ccagttccaa                                              20

<210> SEQ ID NO 3
<211> LENGTH: 20
<212> TYPE: DNA
<213> ORGANISM: Artificial Sequence
<220> FEATURE:
<223> OTHER INFORMATION: hANF Forward Primer

<400> SEQUENCE: 3
aatcaagttc agaggatggg                                              20

<210> SEQ ID NO 4
<211> LENGTH: 20
<212> TYPE: DNA
<213> ORGANISM: Artificial Sequence
<220> FEATURE:
<223> OTHER INFORMATION: hANF Reverse Primer

<400> SEQUENCE: 4
aatgcatggg gtgggagagg                                              20

<210> SEQ ID NO 5
<211> LENGTH: 18
<212> TYPE: DNA
<213> ORGANISM: Artificial Sequence
<220> FEATURE:
<223> OTHER INFORMATION: hVE-Cad Forward Primer

<400> SEQUENCE: 5
```

```
tctctgtcct ctgcacaa                                                18
```

<210> SEQ ID NO 6
<211> LENGTH: 18
<212> TYPE: DNA
<213> ORGANISM: Artificial Sequence
<220> FEATURE:
<223> OTHER INFORMATION: hVe-Cad Reverse Primer

<400> SEQUENCE: 6

```
atgcagaggc tcatgatg                                                18
```

<210> SEQ ID NO 7
<211> LENGTH: 20
<212> TYPE: DNA
<213> ORGANISM: Artificial Sequence
<220> FEATURE:
<223> OTHER INFORMATION: hGAPDH Forward Primer

<400> SEQUENCE: 7

```
gaagagccaa ggacaggtac                                              20
```

<210> SEQ ID NO 8
<211> LENGTH: 20
<212> TYPE: DNA
<213> ORGANISM: Artificial Sequence
<220> FEATURE:
<223> OTHER INFORMATION: hGAPDH Reverse Primer

<400> SEQUENCE: 8

```
ctgcaccacc aactgcttag                                              20
```

<210> SEQ ID NO 9
<211> LENGTH: 24
<212> TYPE: DNA
<213> ORGANISM: Artificial Sequence
<220> FEATURE:
<223> OTHER INFORMATION: mMHC Forward Primer

<400> SEQUENCE: 9

```
gaagagtgag cggcgcatca agga                                         24
```

<210> SEQ ID NO 10
<211> LENGTH: 23
<212> TYPE: DNA
<213> ORGANISM: Artificial Sequence
<220> FEATURE:
<223> OTHER INFORMATION: mMHC Reverse Primer

<400> SEQUENCE: 10

```
tctgctggag aggttattcc tcg                                          23
```

<210> SEQ ID NO 11
<211> LENGTH: 24
<212> TYPE: DNA
<213> ORGANISM: Artificial Sequence
<220> FEATURE:
<223> OTHER INFORMATION: mCardiac Actin Forward Primer

<400> SEQUENCE: 11

```
tgttacgtcg ccttggattt tgag                                         24
```

<210> SEQ ID NO 12
<211> LENGTH: 22
<212> TYPE: DNA
<213> ORGANISM: Artificial Sequence

```
<220> FEATURE:
<223> OTHER INFORMATION: mCardiac Actin Reverse Primer

<400> SEQUENCE: 12
aagagagaga catatcagaa gc                                          22

<210> SEQ ID NO 13
<211> LENGTH: 20
<212> TYPE: DNA
<213> ORGANISM: Artificial Sequence
<220> FEATURE:
<223> OTHER INFORMATION: mCardiac TnC Forward Primer

<400> SEQUENCE: 13
aatggatgac atctacaaag                                             20

<210> SEQ ID NO 14
<211> LENGTH: 20
<212> TYPE: DNA
<213> ORGANISM: Artificial Sequence
<220> FEATURE:
<223> OTHER INFORMATION: mCardiac TnC Reverse Primer

<400> SEQUENCE: 14
tgagctcttc aatgtcatct                                             20

<210> SEQ ID NO 15
<211> LENGTH: 20
<212> TYPE: DNA
<213> ORGANISM: Artificial Sequence
<220> FEATURE:
<223> OTHER INFORMATION: mGAPDH Forward Primer

<400> SEQUENCE: 15
cctctggaaa gctgtggcgt                                             20

<210> SEQ ID NO 16
<211> LENGTH: 20
<212> TYPE: DNA
<213> ORGANISM: Artificial Sequence
<220> FEATURE:
<223> OTHER INFORMATION: mGAPDH Reverse Primer

<400> SEQUENCE: 16
ttggaggcca tgtaggccat                                             20
```